US008404933B2

(12) United States Patent
Chen et al.

(10) Patent No.: US 8,404,933 B2
(45) Date of Patent: Mar. 26, 2013

(54) HERBICIDE RESISTANCE GENE

(75) Inventors: Feng Chen, Knoxville, TN (US); Nan Zhao, Knoxville, TN (US); Gregory Russell Armel, Knoxville, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 343 days.

(21) Appl. No.: 12/701,973

(22) Filed: Feb. 8, 2010

(65) Prior Publication Data

US 2010/0205696 A1 Aug. 12, 2010

Related U.S. Application Data

(60) Provisional application No. 61/150,356, filed on Feb. 6, 2009, provisional application No. 61/224,715, filed on Jul. 10, 2009.

(51) Int. Cl.
*C12N 15/82* (2006.01)
(52) U.S. Cl. ............... 800/300; 435/320.1; 435/419; 435/468
(58) Field of Classification Search ................. None
See application file for complete search history.

(56) References Cited

U.S. PATENT DOCUMENTS

2011/0167523 A1 7/2011 Chen et al.

FOREIGN PATENT DOCUMENTS

| WO | WO 03/016482 | 2/2003 |
| WO | WO 2007/120706 | 10/2007 |

OTHER PUBLICATIONS

Tuskan et al 2006, Science 313: 1596-1604.*
Zhao, N. et al. "Molecular cloning and biochemical characterization of indole-3-acetic acid methyltransferase from poplar" *Phytochemistry*, 2007, pp. 1537-1544, vol. 68.
Zubieta, C. et al. "Structural Basis for Substrate Recognition in the Salicylic Acid Carboxyl Methyltransferase Family" *The Plant Cell*, Aug. 2003, pp. 1704-1716, vol. 15.
Zhao, N. et al. "Structural, Biochemical, and Phylogenetic Analyses Suggest That Indole-3-Acetic Acid Methyltransferase Is an Evolutionarily Ancient Member of the SABATH Family" *Plant Physiology*, Feb. 2008, pp. 455-467, vol. 146.
Soo Seo, H. et al. "Jasomonic acid carboxyl methyltransferase: A key enzyme for jasmonate-regulated plant responses" *PNAS*, Apr. 10, 2001, pp. 4788-4793, vol. 98, No. 8.

* cited by examiner

*Primary Examiner* — David H Kruse
(74) *Attorney, Agent, or Firm* — Saliwanchik, Lloyd & Eisenschenk

(57) ABSTRACT

The subject invention provides novel polynucleotides and polypeptides encoding a methyltransferase. The subject invention provides novel plants that express the methyltrasferase disclosed herein and are resistant to auxin-based herbicides. The subject invention also provides transgenic plants have been transformed with one or more other herbicide resistance genes such that the plants are resistant to the application of auxin-based herbicides and one or more other herbicides.

40 Claims, 6 Drawing Sheets

MEVMQVLHMNKGDDENSYAKNSKVQSKIISLGKRINE

EAIMQMLCSNIPDIMGIADLGCSSGPNSLSVISEITD

IIYAKCRELGRPTPELKVFLNDLPHNDFNFIFGSLPA

FYDKLKKEKGSDFGPCFVSATPGSFYGRLFPSRSLHC

VHSSSSLHWLSQVPAGLESNARTAMNKGKIYISKSSS

LCVLEAYSLQFQKDFSSFLKSRSKEIVPGGCMLLSFM

GRRSTDPTTDESCYHWELLAQALMSMVSEGLVEKEKV

DSFNAPYYGPCVEEMRLEIEKDGSFSVNRLETFEIDW

DGGVDDVDTTSGAALRGQRVAKTIRAVVESMLESHFG

KDIMDELFRRYGEMVEGYLSKTGTKYTILVISMVRN

Fig. 3

- ACCase inhibitors (inhibitors of Acetyl Co-enzyme A carboxylase- graminicides)- specific chemical classes the fops
  - chlorazifop, clodinafop, clofop, cyhalofop, diclofop, fenoxaprop, fluazifop, haloxyfop, isoxapyrifop, metamifop, propaquizafop, quizalofop and trifop.
- EPSP synthase inhibitor
  - glyphosate
- Glutamine synthetase inhibitor
  - bialaphos, glufosinate
- ALS-inhibitors (Acetolactate synthase inhibitors)- members of at least three chemical classes
  - Sulfonylureas: chlorimuron-ethyl, thifensulfuron-ethyl, tribenuron-methyl, primisulfuron, iodosulfuron, triflusulfuron-methyl, halosulfuron-methyl, ethametsulfuron, pyrazosulfuron-ethyl, bensulfuron-methyl, flupyrsulfuron-methyl, other?
  - Pyrimidinylthiobenzoates: bispyribac, pyrithiobac, pyriminobac-methyl
  - Imidazolinones: imazapyr, imazapic, imazamethabenz, imazamox
  - Sulfonyl-amino-carbonyl triazolinones: propoxycarbazone
- Auxin Transport Inhibitors
  - diflufenzopyr, naptalam
- Inhibitors of Photosystem II
  - Phenylcarbamates: Phenmedipham, desmedipham
- PPO-inhibitors
  - Phenyl pyrazoles: pyraflufen-ethyl, fluazolate
  - N-phenyl phthalimides: flu miclorac-pentyl, cinidon-ethylithiadiazoles: fluthiacet-methyl
- DHP inhibitor
  - asulam

Fig. 4

SEQUENCE LISTING

```
<160> NUMBER OF SEQ ID NOS: 2

<210> SEQ ID NO 1
<211> LENGTH: 1110
<212> TYPE: DNA
<213> ORGANISM: poplar trees
<220> FEATURE:
<221> NAME/KEY: CDS
<222> LOCATION: (1)..(1110)
```

```
<400> SEQUENCE: 1 atg gaa gta atg caa gtg ctt cac atg aac aaa gga gat gat gaa aat      48
Met Glu Val Met Gln Val Leu His Met Asn Lys Gly Asp Asp Glu Asn
1               5                   10                  15 agt tat gca aaa aac tcg aaa gtg cag agc aag ata ata tct cta gga      96
Ser Tyr Ala Lys Asn Ser Lys Val Gln Ser Lys Ile Ile Ser Leu Gly
            20                  25                  30 aag cga atc aat gag gag gct ata atg caa atg ttg tgc agc aat atc     144
Lys Arg Ile Asn Glu Glu Ala Ile Met Gln Met Leu Cys Ser Asn Ile
        35                  40                  45 cct gac atc atg ggt att gca gac ctg ggt tgc tcc tct gga cct aac     192
Pro Asp Ile Met Gly Ile Ala Asp Leu Gly Cys Ser Ser Gly Pro Asn
    50                  55                  60 tcg ttg tca gtg atc tcc gaa att act gat atc atc tat gcc aaa tgc     240
Ser Leu Ser Val Ile Ser Glu Ile Thr Asp Ile Ile Tyr Ala Lys Cys
65                  70                  75                  80 aga gag ttg ggt cgt cca aca cca gaa ctt aag gtc ttc ctg aat gat     288
Arg Glu Leu Gly Arg Pro Thr Pro Glu Leu Lys Val Phe Leu Asn Asp
                85                  90                  95 ctt cct cat aat gac ttc aat ttt att ttt gga tcc ttg cca gca ttc     336
Leu Pro His Asn Asp Phe Asn Phe Ile Phe Gly Ser Leu Pro Ala Phe
            100                 105                 110 tat gat aaa tta aag aaa gaa aag ggt tcc gac ttc ggg cca tgc ttt     384
Tyr Asp Lys Leu Lys Lys Glu Lys Gly Ser Asp Phe Gly Pro Cys Phe
        115                 120                 125 gta tca gca acg ccg ggt tct ttc tat ggt aga ttg ttt cct agc agg     432
Val Ser Ala Thr Pro Gly Ser Phe Tyr Gly Arg Leu Phe Pro Ser Arg
    130                 135                 140 agc ttg cat tgt gtg cac tct tct tct agt ctt cac tgg ctc tcg cag     480
Ser Leu His Cys Val His Ser Ser Ser Ser Leu His Trp Leu Ser Gln
145                 150                 155                 160 gtt cca gct ggt cta gag agc aac gcg agg acg gcc atg aac aag gga     528
Val Pro Ala Gly Leu Glu Ser Asn Ala Arg Thr Ala Met Asn Lys Gly
                165                 170                 175 aag att tat ata tca aag tca agc tcg ctt tgt gtg tta gaa gca tat     576
Lys Ile Tyr Ile Ser Lys Ser Ser Ser Leu Cys Val Leu Glu Ala Tyr
            180                 185                 190 tca ttg cag ttt caa aaa gac ttt tcg tcg ttt cta aaa tca cgt tcg     624
Ser Leu Gln Phe Gln Lys Asp Phe Ser Ser Phe Leu Lys Ser Arg Ser
        195                 200                 205 aag gaa att gtt ccc gga ggc tgc atg ctc ttg tca ttc atg ggc agg     672
Lys Glu Ile Val Pro Gly Gly Cys Met Leu Leu Ser Phe Met Gly Arg
    210                 215                 220 aga tct acc gat ccc acc acg gac gag agt tgc tac cat tgg gag ctc     720
Arg Ser Thr Asp Pro Thr Thr Asp Glu Ser Cys Tyr His Trp Glu Leu
225                 230                 235                 240 tta gca cag gca cta atg agc atg gtt tct gag ggg ctc gtc gag aaa     768
Leu Ala Gln Ala Leu Met Ser Met Val Ser Glu Gly Leu Val Glu Lys
                245                 250                 255 gaa aag gtc gat tcc ttt aac gcc ccc tac tat ggt cca tgt gtg gaa     816
Glu Lys Val Asp Ser Phe Asn Ala Pro Tyr Tyr Gly Pro Cys Val Glu
            260                 265                 270 gaa atg agg tta gag att gaa aag gat ggt tct ttc agt gtc aat cgg     864
Glu Met Arg Leu Glu Ile Glu Lys Asp Gly Ser Phe Ser Val Asn Arg
        275                 280                 285 ctc gag acc ttt gaa att gac tgg gat gga ggt gtc gac gat gtg gac     912
Leu Glu Thr Phe Glu Ile Asp Trp Asp Gly Gly Val Asp Asp Val Asp
    290                 295                 300 acc acg tct ggg gca gca tta cgt gga cag aga gtg gcc aag aca atc     960
Thr Thr Ser Gly Ala Ala Leu Arg Gly Gln Arg Val Ala Lys Thr Ile
```

```
Thr Thr Ser Gly Ala Ala Leu Arg Gly Gln Arg Val Ala Lys Thr Ile
305                 310                 315                 320 aga gct gtc gtg gag tcg atg ctg gaa tct cat ttt ggg aag gac ata         1008
Arg Ala Val Val Glu Ser Met Leu Glu Ser His Phe Gly Lys Asp Ile
                325                 330                 335 atg gac gaa tta ttt cga agg tat gga gag atg gtg gag ggt tac ttg         1056
Met Asp Glu Leu Phe Arg Arg Tyr Gly Glu Met Val Glu Gly Tyr Leu
            340                 345                 350 tca aag acc gga acc aag tac acc atc ttg gtc att tca atg gtt aga         1104
Ser Lys Thr Gly Thr Lys Tyr Thr Ile Leu Val Ile Ser Met Val Arg
        355                 360                 365 aat taa                                                                 1110
Asn <210> SEQ ID NO 2
<211> LENGTH: 369
<212> TYPE: PRT
<213> ORGANISM: poplar trees

<400> SEQUENCE: 2

Met Glu Val Met Gln Val Leu His Met Asn Lys Gly Asp Asp Glu Asn
1               5                   10                  15

Ser Tyr Ala Lys Asn Ser Lys Val Gln Ser Lys Ile Ile Ser Leu Gly
            20                  25                  30

Lys Arg Ile Asn Glu Glu Ala Ile Met Gln Met Leu Cys Ser Asn Ile
        35                  40                  45

Pro Asp Ile Met Gly Ile Ala Asp Leu Gly Cys Ser Ser Gly Pro Asn
    50                  55                  60

Ser Leu Ser Val Ile Ser Glu Ile Thr Asp Ile Ile Tyr Ala Lys Cys
65                  70                  75                  80

Arg Glu Leu Gly Arg Pro Thr Pro Glu Leu Lys Val Phe Leu Asn Asp
                85                  90                  95

Leu Pro His Asn Asp Phe Asn Phe Ile Phe Gly Ser Leu Pro Ala Phe
            100                 105                 110

Tyr Asp Lys Leu Lys Lys Glu Lys Gly Ser Asp Phe Gly Pro Cys Phe
        115                 120                 125

Val Ser Ala Thr Pro Gly Ser Phe Tyr Gly Arg Leu Phe Pro Ser Arg
    130                 135                 140

Ser Leu His Cys Val His Ser Ser Ser Ser Leu His Trp Leu Ser Gln
145                 150                 155                 160

Val Pro Ala Gly Leu Glu Ser Asn Ala Arg Thr Ala Met Asn Lys Gly
                165                 170                 175

Lys Ile Tyr Ile Ser Lys Ser Ser Ser Leu Cys Val Leu Glu Ala Tyr
            180                 185                 190

Ser Leu Gln Phe Gln Lys Asp Phe Ser Ser Phe Leu Lys Ser Arg Ser
        195                 200                 205

Lys Glu Ile Val Pro Gly Gly Cys Met Leu Leu Ser Phe Met Gly Arg
    210                 215                 220

Arg Ser Thr Asp Pro Thr Thr Asp Glu Ser Cys Tyr His Trp Glu Leu
225                 230                 235                 240

Leu Ala Gln Ala Leu Met Ser Met Val Ser Glu Gly Leu Val Glu Lys
                245                 250                 255

Glu Lys Val Asp Ser Phe Asn Ala Pro Tyr Tyr Gly Pro Cys Val Glu
            260                 265                 270

Glu Met Arg Leu Glu Ile Glu Lys Asp Gly Ser Phe Ser Val Asn Arg
        275                 280                 285
```

-continued

```
Leu Glu Thr Phe Glu Ile Asp Trp Asp Gly Val Asp Asp Val Asp
    290             295             300

Thr Thr Ser Gly Ala Ala Leu Arg Gly Gln Arg Val Ala Lys Thr Ile
305             310             315                     320

Arg Ala Val Val Glu Ser Met Leu Glu Ser His Phe Gly Lys Asp Ile
                325             330                 335

Met Asp Glu Leu Phe Arg Arg Tyr Gly Glu Met Val Glu Gly Tyr Leu
            340             345             350

Ser Lys Thr Gly Thr Lys Tyr Thr Ile Leu Val Ile Ser Met Val Arg
        355             360             365

Asn
```

HERBICIDE RESISTANCE GENE

CROSS-REFERENCE TO RELATED APPLICATIONS

This application claims the benefit of U.S. Provisional Application Ser. No. 61/150,356, filed Feb. 6, 2009 and U.S. Provisional Application Ser. No. 61/224,715, filed Jul. 10, 2009, the disclosures of which are hereby incorporated by reference in their entirety, including all figures, tables and amino acid or nucleic acid sequences.

BACKGROUND OF THE INVENTION

There are many different types of herbicides presently used for the control of weeds. One extremely popular herbicide is glyphosate. Crops, such as corn, soybeans, canola, cotton, sugar beets, wheat, turf, and rice, have been developed that are resistant to glyphosate. Thus, fields with actively growing glyphosate resistant soybeans, for example, can be sprayed to control weeds without significantly damaging the soybean plants.

With the introduction of genetically engineered, glyphosate tolerant crops (GTCs) in the mid-1990's, growers were enabled with a simple, convenient, flexible, and inexpensive tool for controlling a wide spectrum of broadleaf and grass weeds unparalleled in agriculture. Consequently, producers were quick to adopt GTCs and in many instances abandon many of the accepted best agronomic practices such as crop rotation, herbicide mode of action rotation, tank mixing, incorporation of mechanical with chemical and cultural weed control. Currently glyphosate tolerant soybean, cotton, corn, and canola are commercially available in the United States and elsewhere.

Alfalfa was the first perennial GTC introduced, furthering the opportunity for repeated use of glyphosate on the same crop and fields repeatedly over a period of years. More GTCs (e.g., wheat, rice, sugar beets, turf, etc.) are poised for introduction pending global market acceptance. Many other glyphosate resistant species are in experimental to development stages (e.g., sugar cane, sunflower, beets, peas, carrot, cucumber, lettuce, onion, strawberry, tomato, and tobacco; forestry species like poplar and sweetgum; and horticultural species like marigold, petunia, and begonias; see "isb.vt.edu/cfdocs/fieldtests1.cfm, 2005" website). Additionally, the cost of glyphosate has dropped dramatically in recent years to the point that few conventional weed control programs can effectively compete on price and performance with glyphosate GTC systems.

In areas where growers are faced with glyphosate resistant weeds or a shift to more difficult-to-control weed species, growers can compensate for glyphosate's weaknesses by tank mixing or alternating with other herbicides that will control the missed weeds. One popular tankmix partner for controlling broadleaf escapes in many instances has been 2,4-dichlorophenoxyacetic acid (2,4-D). 2,4-D has been used agronomically and in non-crop situations for broad spectrum, broadleaf weed control for more than 60 years. Individual cases of more tolerant species have been reported, but 2,4-D remains one of the most widely used herbicides. A limitation to further use of 2,4-D is that its selectivity in dicot crops like soybean or cotton is very poor, and hence 2,4-D is not typically used on (and generally not near) sensitive dicot crops. Additionally, 2,4-D's use in grass crops is somewhat limited by the nature of crop injury that can occur. 2,4-D in combination with glyphosate has been used to provide a more robust burndown treatment prior to planting no-till soybeans and cotton; however, due to these dicot species' sensitivity to 2,4-D, these burndown treatments must occur at least 14-30 days prior to planting.

BRIEF SUMMARY OF THE INVENTION

The subject invention provides novel plants that are resistant to auxin-based herbicides, such as 2,4-D. In some aspects of the invention, the plants disclosed herein are also resistant to other herbicides. In these aspects of the invention, heterologous glyphosate-, ALS- (imidazolinone, sulfonylurea), aryloxyalkanoate-, HPPD-, PPO-, and/or glufosinate-resistance genes can also be introduced into a plant to provide tolerance to a variety of herbicides. Various other aspects of the invention provide nucleic acid and polypeptide sequences encoding a methyltransferase that can be used to inactivate auxin-based herbicides.

BRIEF DESCRIPTION OF THE SEQUENCES

SEQ ID NO:1 is the nucleic acid sequence that encodes the methyltransferase PtJBMT3.

SEQ ID NO:2 is the translated protein sequence encoded by SEQ ID NO:1.

BRIEF DESCRIPTION OF THE TABLES

Table 1: Exemplary commercially available auxin-based herbicides.

Table 2: Relative assay activities of PtJBMT and PtJBMTm3 with auxin-based herbicides.

Table 3: Amino acid substitution table.

BRIEF DESCRIPTION OF THE FIGURES

FIG. 3. Sequence of PtJBMTm3 (SEQ ID NO: 1). Active site residues are in bold and double underlined.

FIG. 4. Additional possible herbicide substrates for PtJBMTm3.

A) A represents N or $CR_5$;

$R_1$ represents $C_1$-$C_4$ alkyl, $C_1$-$C_4$ haloalkyl, $C_2$-$C_4$ alkoxyalkyl, $C_2$-$C_4$ alkythioalkyl, $C_2$-$C_4$ alkenyl, $C_2$-$C_4$ haloalkenyl, $C_2$-$C_4$ alkoxyalkenyl, $C_2$-$C_4$ thioalkylalkenyl, $C_2$-$C_4$ alkynyl or $C_2$-$C_4$ haloalkynyl, formyl, $C_2$-$C_4$ alkylcarbonyl, $C_2$-$C_4$ haloalkylcarbonyl;

$R_2$ represents $C_1$-$C_6$ alkyl, $C_1$-$C_6$ haloalkyl, $C_2$-$C_6$ alkenyl, $C_2$-$C_6$ haloalkenyl or

Figure 6:
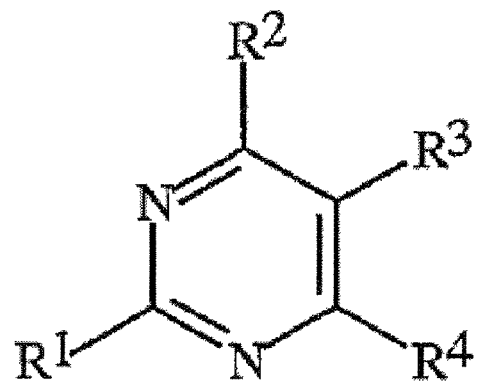

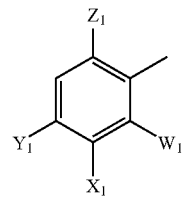

wherein
W$_1$ represents H or halogen;
X$_1$ represents H, halogen, nitro, cyano, formyl, C$_1$-C$_6$ alkyl, C$_2$-C$_6$ alkenyl, C$_2$-C$_6$ alkynyl, C$_1$-C$_6$ alkoxy, C$_2$-C$_4$ alkoxyalkyl, C$_2$-C$_6$ alkylcarbonyl, C$_1$-C$_6$ alkythio, C$_1$-C$_6$ alkylsulfinyl, C$_1$-C$_6$ alkylsulfonyl, C$_2$-C$_4$ alkenyloxy, C$_2$-C$_4$ alkenyloxy, C$_2$-C$_4$ alkenylthio, C$_2$-C$_4$ alkynylthio, C$_1$-C$_6$ haloalkyl, C$_2$-C$_6$ haloalkenyl, C$_2$-C$_6$ haloalkynyl, C$_1$-C$_6$ haloalkoxy, C$_2$-C$_4$ haloalkoxyalkyl, C$_2$-C$_6$ haloalkylcarbonyl, C$_1$-C$_6$ haloalkylthio, C$_1$-C$_6$ haloalkylsulfinyl, C$_1$-C$_6$ haloalkylsulfonyl, C$_3$-C$_6$ trialkylsilyl, C$_2$-C$_4$ haloalkenyloxy, C$_2$-C$_4$ haloalkynyloxy, C$_2$-C$_4$ haloalkenylthio, C$_2$-C$_4$ haloalkynylthio, —C(O)OR$_7$, —C(O)NR$_6$R$_7$, —CR$_6$NOR$_7$, —NR$_6$R$_7$, —NR$_6$OR$_7$, —NR$_6$SO$_2$R$_7$, —NR$_6$C(O)R$_7$, —NR$_6$C(O)OR$_7$, —NR$_6$C(O)NR$_6$R$_7$ or —NCR$_6$NR$_6$R$_7$;
Y$_1$ represents H, halogen, C$_1$-C$_6$ alkyl, C$_1$-C$_6$ haloalkyl, C$_1$-C$_6$ alkoxy, C$_1$-C$_6$ haloalkoxy, C$_2$-C$_6$ alkenyl or C$_2$-C$_6$ haloalkenyl, or, when X$_i$ and Y$_i$ are taken together, represents —O(CH$_2$)$_n$CH$_2$—, or —O(CH$_2$)$_n$O— wherein n=1 or 2; and
Z$_1$ represents H or halogen;
R$_3$ and R$_4$ independently represent H, C$_1$-C$_6$ alkyl, C$_3$-C$_6$ alkenyl, C$_3$-C$_6$ alkynyl, hydroxy, C$_1$-C$_6$ alkoxy, amino, C$_1$-C$_6$ acyl, C$_1$-C$_6$ carboalkoxy, C$_1$-C$_6$ alkylcarbamyl, C$_1$-C$_6$ alkylsulfonyl, C$_1$-C$_6$ trialkylsilyl or C$_1$-C$_6$ dialkyl phosphonyl or R$_3$ and R$_4$ taken together with N represent a 5- or 6-membered saturated ring; and
R$_5$ represents H or halogen;
R$_6$ represents H, C$_1$-C$_4$ alkyl or C$_1$-C$_4$ haloalkyl; and
R$_7$ represents C$_1$-C$_4$ alkyl or C$_1$-C$_4$ haloalkyl;
and agriculturally acceptable derivatives of the carboxylic acid group;
B) a compound as set forth in A, wherein R$_3$ and R$_4$ independently represent H or C$_1$-C$_6$ alkyl;
C) a compound as set forth in A or B in which the agriculturally acceptable derivatives of the carboxylic acid group are agriculturally acceptable salts, esters and amides;
D) a compound as set forth in A, or B or C, in which R$_1$ is C$_1$-C$_2$ alkyl, C$_1$-C$_2$ haloalkyl, C$_2$-C$_3$ alkenyl or C$_2$-C$_3$ haloalkenyl;
E) a compound as set forth in D, in which R$_1$ is vinyl;
F) a compound as set forth in any one of A, B, C, D or E in which R$_2$ is cyclopropyl;
G) as set forth in any one of A, B, C, D or E in which R$_2$ is wherein
W$_1$ represents H or halogen;
X$_1$ represents H, halogen, nitro, cyano, formyl, C$_1$-C$_6$ alkyl, C$_2$-C$_6$ alkenyl, C$_2$-C$_6$ alkynyl, C$_1$-C$_6$ alkoxy, C$_2$-C$_4$ alkoxyalkyl, C$_2$-C$_6$ alkylcarbonyl, C$_1$-C$_6$ alkythio, C$_1$-C$_6$ alkylsulfinyl, C$_1$-C$_6$ alkylsulfonyl, C$_2$-C$_4$ alkenyloxy, C$_2$-C$_4$ alkynloxy, C$_2$-C$_4$ alkenylthio, C$_2$-C$_4$ alkynylthio, C$_1$-C$_6$ haloalkyl, C$_2$-C$_6$ haloalkenyl, C$_2$-C$_6$ haloalkynyl, C$_1$-C$_6$ haloalkoxy, C$_2$-C$_4$ haloalkoxyalkyl, C$_2$-C$_6$ haloalkylcarbonyl, C$_1$-C$_6$ haloalkythio, C$_1$-C$_6$ haloalkylsulfinyl, C$_1$-C$_6$ haloalkylsulfonyl, C$_3$-C$_6$ trialkylsilyl, C$_2$-C$_4$ haloalkenyloxy, C$_2$-C$_4$ haloalkynyloxy, C$_2$-C$_4$ haloalkenylthio, C$_2$-C$_4$ haloalkynylthio, —C(O)OR$_7$, —C(O)NR$_6$R$_7$, —CR$_6$NOR$_7$, —NR$_6$R$_7$, —NR$_6$OR$_7$, —NR$_6$SO$_2$R$_7$, —NR$_6$C(O)R$_7$, —NR$_6$C(O)OR$_7$, —NR$_6$C(O)NR$_6$R$_7$ or —NCR$_6$NR$_6$R$_7$;
Y$_1$ represents H, halogen, C$_1$-C$_6$ alkyl, C$_1$-C$_6$ haloalkyl, C$_1$-C$_6$ alkoxy, C$_1$-C$_6$ haloalkoxy, C$_2$-C$_6$ alkenyl or C$_2$-C$_6$ haloalkenyl, or, when X$_1$ and Y$_1$ are taken together, represents —O(CH$_2$)—CH$_2$—, or —O(CH$_2$)$_n$O— wherein n=1 or 2; and
Z$_1$ represents H or halogen;
R$_5$ represents H or halogen;
R$_6$ represents H, C$_1$-C$_4$ alkyl or C$_1$-C$_4$ haloalkyl; and
R$_7$ represents C$_1$-C$_4$ alkyl or C$_1$-C$_4$ haloalkyl;
H) a compound as set forth in H, in which W$_i$ represents H or F, X$_1$ represents II, halogen, C$_1$-C$_1$ alkyl, C$_1$-C$_4$ haloalkyl, alkoxy, C$_1$-C$_4$ haloalkoxy or —NR$_6$R$_7$, Y$_1$ represents C$_1$ or halomethyl, and Z$_1$ represents H or F;
I) a compound having the formula in which
W$_1$ represents H or F;
X$_1$ represents H, halogen, C$_1$-C$_4$ alkyl, C$_1$-C$_4$ haloalkyl, C$_1$-C$_4$ alkoxy, C$_1$-C$_4$ haloalkoxy or —NR$_6$R$_7$;
Y$_1$ represents C$_1$ or halomethyl;
Z$_1$ represents H or F; and agriculturally acceptable derivatives of the carboxylic acid group; or
J) a compound having the formula in which
W$_1$ represents H or F;
X$_1$ represents H, halogen, C$_1$-C$_4$ alkyl, C$_1$-C$_4$ haloalkyl, C$_1$-C$_4$ alkoxy, C$_1$-C$_4$ haloalkoxy or —NR$_6$R$_7$;
Y$_1$ represents Cl or halomethyl;
Z$_1$ represents H or F; and agriculturally acceptable derivatives of the carboxylic acid group.
FIG. 6. Exemplary auxin-based herbicides disclosed in WO/2005/063721. The various substituents and compounds embraced by the structure are as follows:
A) R$_1$ is cyclopropyl optionally substituted with 1-5 R$^5$, isopropyl optionally substituted with 1-5 R$^6$, or phenyl optionally substituted with 1-3 R$^7$;
R$^2$ is ((O))$_j$C(R$^{15}$)(R$^{16}$))$_k$R;
R is CO$_2$H or a herbicidally effective derivative of CO$_2$H;
R$^3$ is halogen, cyano, nitro, OR$^{20}$, SR$^{21}$ or N(R$^{22}$)R$^{23}$;

$R^4$ is —N($R^{24}$)$R^{25}$ or —NO$_2$;

each $R^5$ and $R^6$ is independently halogen, $C_1$-$C_6$ alkyl, $C_1$-$C_6$ haloalkyl, $C_2$-$C_6$ alkenyl, $C_2$-$C_6$ haloalkenyl, $C_1$-$C_3$ alkoxy, $C_1$-$C_2$ haloalkoxy, $C_1$-$C_3$ alkylthio or $C_1$-$C_2$ haloalkylthio;

each $R^7$ is independently halogen, cyano, nitro, $C_1$-$C_4$ alkyl, $C_1$-$C_4$ haloalkyl, $C_3$-$C_6$ cycloalkyl, $C_3$-$C_6$ halocycloalkyl, $C_1$-$C_4$ hydroxyalkyl, $C_2$-$C_4$ alkoxyalkyl, $C_2$-$C_4$ haloalkoxyalkyl, $C_2$-$C_4$ alkenyl, $C_2$-$C_4$ haloalkenyl, $C_3$-$C_4$ alkynyl, $C_3$-$C_4$ haloalkynyl, hydroxy, $C_1$-$C_4$ alkoxy, $C_1$-$C_4$ haloalkoxy, $C_2$-$C_4$ alkenyloxy, $C_2$-$C_4$ haloalkenyloxy, $C_2$-$C_4$ alkynyloxy, $C_3$-$C_4$ haloalkynyloxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_2$-$C_4$ alkenylthio, $C_2$-$C_4$ haloalkenylthio, $C_2$-$C_4$ alkenylsulfinyl, $C_2$-$C_4$ haloalkenylsulfinyl, $C_2$-$C_4$ alkenylsulfonyl, $C_2$-$C_4$ haloalkenylsulfonyl, $C_3$-$C_4$ alkynylthio, $C_3$-$C_4$ haloalkynylthio, $C_3$-$C_4$ alkynylsulfinyl, $C_3$-$C_4$ haloalkynylsulfinyl, $C_3$-$C_4$ alkynylsulfonyl, $C_3$-$C_4$ haloalkynylsulfonyl, $C_1$-$C_4$ alkylamino, $C_2$-$C_8$ dialkylamino, $C_3$-$C_6$ cycloalkylamino, $C_4$-$C_6$ (alkyl)cycloalkylamino, $C_2$-$C_6$ alkylcarbonyl, $C_2$-$C_6$ alkoxycarbonyl, $C_2$-$C_6$ alkylaminocarbonyl, $C_3$-$C_8$ dialkylaminocarbonyl, $C_3$-$C_6$ trialkylsilyl, phenyl, phenoxy and 5- or 6-membered heteroaromatic rings, each phenyl, phenoxy and 5- or 6-membered heteroaromatic ring optionally substituted with one to three substituents independently selected from $R^{45}$; or two adjacent $R_7$ are taken together as —OCH$_2$O—, —CH$_2$CH$_2$O—, —OCH(CH$_3$)O—, —OC(CH$_3$)$_2$O—, —OCF$_2$O—, —CF$_2$CF$_2$O—, —OCF$_2$CF$_2$O— or —CH=CH—CH=CH—; $R^{15}$ is H, halogen, $C_1$-$C_4$ alkyl, $C_1$-$C_4$ haloalkyl, hydroxy, $C_1$-$C_4$ alkoxy or $C_2$-$C_4$ alkylcarbonyloxy;

$R^{16}$ is H, halogen, $C_1$-$C_4$ alkyl or $C_1$-$C_4$ haloalkyl; or $R^{15}$ and $R^{16}$ are taken together as an oxygen atom to form, with the carbon atom to which they are attached, a carbonyl moiety;

$R^{20}$ is H, $C_1$-$C_4$ alkyl or $C_1$-$C_3$ haloalkyl;

$R^{21}$ is H, $C_1$-$C_4$ alkyl or $C_1$-$C_3$ haloalkyl;

$R^{22}$ and $R^{23}$ are independently H or $C_1$-$C_4$ alkyl;

$R^{24}$ is H, $C_1$-$C_4$ alkyl optionally substituted with 1-2 $R^{30}$, $C_2$-$C_4$ alkenyl optionally substituted with 1-2 $R^{31}$, or $C_2$-$C_4$ alkynyl optionally substituted with 1-2 $R^{32}$; or $R^{24}$ is C(=O)$R^{33}$, nitro, O$R^{34}$, S(O)$_2R^{35}$, N($R^{36}$)$R^{37}$ or N=C($R^{62}$)$R^{63}$;

$R^{25}$ is H, $C_1$-$C_4$ alkyl optionally substituted with 1-2 $R^{30}$ or C(=O)$R^{33}$; or $R^{24}$ and $R^{25}$ are taken together as a radical selected from —(CH$_2$)$_4$—, —(CH$_2$)$_5$—, —CH$_2$CH=CHCH$_2$— and —(CH$_2$)$_2$—O—(CH$_2$)$_2$—, each radical optionally substituted with 1-2 $R^{38}$; or $R^{24}$ and $R^{25}$ are taken together as =C($R^{39}$)N($R^{40}$)$R^{41}$ or =C($R^{42}$)O$R^{43}$;

each $R^{30}$, $R^{31}$ and $R^{32}$ is independently halogen, $C_1$-$C_3$ alkoxy, $C_1$-$C_3$ haloalkoxy, $C_1$-$C_3$ alkylthio, $C_1$-$C_3$ haloalkylthio, amino, $C_1$-$C_3$ alkylamino, $C_2$-$C_4$ dialkylamino or $C_2$-$C_4$ alkoxycarbonyl;

each $R^{33}$ is independently H, $C_1$-$C_{14}$ alkyl, $C_1$-$C_3$ haloalkyl, $C_1$-$C_4$ alkoxy, phenyl, phenoxy or benzyloxy;

$R^{34}$ is H, $C_1$-$C_4$ alkyl, $C_1$-$C_3$ haloalkyl or CH$R^{66}$C(O)O$R^{67}$;

$R^{35}$ is $C_1$-$C_4$ alkyl or $C_1$-$C_3$ haloalkyl;

$R^{36}$ is H, $C_1$-$C_4$ alkyl or C(=O)$R^{64}$;

$R^{37}$ is H or $C_1$-$C_4$ alkyl;

each $R^{38}$ is independently halogen, $C_1$-$C_3$ alkyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_3$ alkylamino, $C_2$-$C_4$ dialkylamino or $C_2$-$C_4$ alkoxycarbonyl;

$R^{39}$ is H or $C_1$-$C_4$ alkyl;

$R^{40}$ and $R^{41}$ are independently H or $C_1$-$C_4$ alkyl; or $R^{40}$ and $R^{41}$ are taken together as —(CH$_2$)$_4$—, —(CH$_2$)$_5$—, —CH$_2$CH=CHCH$_2$— or —(CH$_2$)$_2$O(CH$_2$)$_2$—;

$R^{42}$ is H or $C_1$-$C_4$ alkyl;

$R^{43}$ is $C_1$-$C_4$ alkyl;

each $R^{45}$ is independently halogen, cyano, nitro, $C_1$-$C_4$ alkyl, $C_1$-$C_4$ haloalkyl, $C_3$-$C_6$ cycloalkyl, $C_3$-$C_6$ halocycloalkyl, $C_2$-$C_4$ alkenyl, $C_2$-$C_4$ haloalkynyl, $C_3$-$C_4$ alkynyl, $C_3$-$C_4$ haloalkynyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_4$-$C_6$ (alkyl)cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;

$R^{62}$ is H, $C_1$-$C_4$ alkyl or phenyl optionally substituted with 1-3 $R^{65}$;

$R^{63}$ is H or $C_1$-$C_4$ alkyl; or $R^{62}$ and $R^{63}$ are taken together as —(CH$_2$)$_4$— or —(CH$_2$)$_5$—;

$R^{64}$ is H, $C_{1-4}$ alkyl, $C_1$-$C_3$ haloalkyl, $C_1$-$C_4$ alkoxy, phenyl, phenoxy or benzyloxy;

each $R^{65}$ is independently CH$_3$, $C_1$ or OCH$_3$;

$R^{66}$ is H, $C_1$-$C_4$ alkyl or $C_1$-$C_4$ alkoxy;

$R^{67}$ is E, $C_1$-$C_4$ alkyl or benzyl;

j is 0 or 1; and k is 0 or 1;

provided that:

(a) when k is 0, then j is 0;

(b) when $R^2$ is CH$_2$O$R^a$ wherein $R^a$ is H, optionally substituted alkyl or benzyl, then $R^3$ is other than cyano;

(c) when $R^1$ is phenyl substituted by Cl in each of the meta positions, the phenyl is also substituted by $R^7$ in the para position;

(d) when $R^1$ is phenyl substituted by $R^7$ in the para position, said $R^7$ is other than tert-butyl, cyano or optionally substituted phenyl;

(e) when $R^1$ is cyclopropyl or isopropyl optionally substituted with 1-5 $R^6$, then R is other than C(=W)N($R^b$)S(O)$_2$—$R^c$—$R^d$ wherein W is O, S, N$R^e$ or NO$R^e$; $R^b$ is hydrogen, $C_1$-$C_4$ alkyl, $C_2$-$C_6$ alkenyl or $C_2$-$C_6$ alkynyl; $R^c$ is a direct bond or CH$R^f$, O, N$R^e$ or NO$R^e$; $R^d$ is an optionally substituted heterocyclic or carbocyclic aromatic radical having 5 to 6 ring atoms, the radical being optionally condensed with an aromatic or nonaromatic 5- or 6-membered ring; each $R^e$ is independently H, $C_1$-$C_3$ alkyl, $C_1$-$C_3$ haloalkyl or phenyl; and $R^f$ is H, $C_1$-$C_3$ alkyl or phenyl; and (f) the compound of Formula I is other than diethyl 6-amino-5-nitro-2-phenyl-4-pyrimidinemalonate;

B) a compound according to A, wherein:

$R^2$ is CO$_2R^{12}$, CH$_2$O$R^{13}$, CH(O$R^{46}$)(O$R^{47}$), CHO, C(=NO$R^{14}$)H, C(=NN$R^{48}R^{49}$)H, (O)$_jC(R^{15}$)($R^{16}$)CO$_2R^{17}$, C(=O)N($R^{18}$)$R^{19}$, C(=S)O$R^{50}$, C(=O)S$R^{51}$, C(=S)S$R^{52}$ or C(=N$R^{53}$)Y$R^{54}$;

$R^{12}$ is H, —CH[C(O)O(CH$_2$)$_m$], —N=C($R^{55}$)$R^{56}$; or a radical selected from $C_1$-$C_{14}$ alkyl, $C_3$-$C_{12}$ cycloalkyl, $C_4$-$C_{12}$ alkylcycloalkyl, $C_4$-$C_{12}$ cycloalkylalkyl, $C_2$-$C_{14}$ alkenyl, $C_2$-$C_{14}$ alkynyl and phenyl, each radical optionally substituted with 1-3 $R_{27}$; or $R^{12}$ is a divalent radical linking the carboxylic ester function CO$_2R^{12}$ of each of two pyrimidine ring systems of Formula I, the divalent radical selected from —CH$_2$—, —(CH$_2$)$_2$—, —(CH$_2$)$_3$— and —CH(CH$_3$)CH$_2$—;

$R^{13}$ is H, $C_1$-$C_{10}$ alkyl optionally substituted with 1-3 $R^{28}$, or benzyl;

$R^{14}$ is H, $C_1$-$C_4$ alkyl, $C_1$-$C_4$ haloalkyl or benzyl;

R$^{17}$ is C$_1$-C$_{10}$ alkyl optionally substituted with 1-3 R$^{29}$, or benzyl;

R$^{18}$ is H, C$_1$-C$_4$ alkyl, hydroxy, C$_1$-C$_4$ alkoxy or S(O)$_2$R$^{57}$;

R$^{19}$ is H or C$_1$-C$_4$ alkyl;

each R$^{27}$ is independently halogen, cyano, hydroxycarbonyl, C$_2$-C$_4$ alkoxycarbonyl, hydroxy, C$_1$-C$_4$ alkoxy, C$_1$-C$_4$ haloalkoxy, C$_1$-C$_4$ alkylthio, C$_1$-C$_4$ haloalkylthio, amino, C$_1$-C$_4$ alkylamino, C$_2$-C$_4$ dialkylamino, —CH[O(CH$_2$)$_n$] or phenyl optionally substituted with 1-3 R$^{44}$; or two R$^{27}$ are taken together as —OC(O)O— or —O(C(R$^{58}$)(R$^{58}$))$_{1-2}$O—; or two R$^{27}$ are taken together as an oxygen atom to form, with the carbon atom to which they are attached, a carbonyl moiety;

each R$^{28}$ is independently halogen, C$_1$-C$_4$ alkoxy, C$_1$-C$_4$ haloalkoxy, C$_1$-C$_4$ alkylthio, C$_1$-C$_4$ haloalkylthio, amino, C$_1$-C$_4$ alkylamino or C$_2$-C$_4$ dialkylamino; or two R$^{28}$ are taken together as an oxygen atom to form, with the carbon atom to which they are attached, a carbonyl moiety;

each R$^{29}$ is independently halogen, C$_1$-C$_4$ alkoxy, C$_1$-C$_4$ haloalkoxy, C$_1$-C$_4$ alkylthio, C$_1$-C$_4$ haloalkylthio, amino, C$_1$-C$_4$ alkylamino or C$_2$-C$_4$ dialkylamino;

each R$^{44}$ is independently halogen, C$_1$-C$_4$ alkyl, C$_1$-C$_3$ haloalkyl, hydroxy, C$_1$-C$_4$ alkoxy, C$_1$-C$_3$ haloalkoxy, C$_1$-C$_3$ alkylthio, C$_1$-C$_3$ haloalkylthio, amino, C$_1$-C$_3$ alkylamino, C$_2$-C$_4$ dialkylamino or nitro;

R$^{46}$ and R$^{47}$ are independently C$_1$-C$_4$ alkyl or C$_1$-C$_3$ haloalkyl; or R$^{46}$ and R$^{47}$ are taken together as —CH$_2$CH$_2$—, —CH$_2$CH(CH$_3$)— or —(CH$_2$)$_3$—;

R$^{48}$ is H, C$_1$-C$_4$ alkyl, C$_1$-C$_4$ haloalkyl, C$_2$-C$_4$ alkylcarbonyl, C$_2$-C$_4$ alkoxycarbonyl or benzyl;

R$^{49}$ is H, C$_1$-C$_4$ alkyl or C$_1$-C$_4$ haloalkyl;

R$^{50}$, R$^{51}$ and R$^{52}$ are H; or a radical selected from C$_1$-C$_{14}$ alkyl, C$_3$-C$_{12}$ cycloalkyl, C$_4$-C$_{12}$ alkylcycloalkyl, C$_4$-C$_{12}$ cycloalkylalkyl, C$_2$-C$_{14}$ alkenyl and C$_2$-C$_{14}$ alkynyl, each radical optionally substituted with 1-3 R$^{27}$;

Y is O, S or NR$^{61}$;

R$^{53}$ is H, C$_1$-C$_3$ alkyl, C$_1$-C$_3$ haloalkyl, C$_2$-C$_4$ alkoxyalkyl, OH or C$_1$-C$_3$ alkoxy;

R$^{54}$ is C$_1$-C$_3$ alkyl, C$_1$-C$_3$ haloalkyl or C$_2$-C$_4$ alkoxyalkyl; or R$^{53}$ and R$^{54}$ are taken together as —(CH$_2$)$_2$—, —CH$_2$CH(CH$_3$)— or —(CH$_2$)$_3$—;

R$^{55}$ and R$^{56}$ are independently C$_1$-C$_4$ alkyl;

R$^{57}$ is C$_1$-C$_4$ alkyl, C$_1$-C$_3$ haloalkyl or NR$^{59}$R$^{60}$;

each R$^{58}$ is independently selected from H and C$_1$-C$_4$ alkyl;

R$^{59}$ and R$^{60}$ are independently H or C$_1$-C$_4$ alkyl;

R$^{61}$ is H, C$_1$-C$_3$ alkyl, C$_1$-C$_3$ haloalkyl or C$_2$-C$_4$ alkoxyalkyl;

m is an integer from 2 to 3; and n is an integer from 1 to 4;

C) a compound according to B, wherein R$^3$ is halogen;

D) a compound according to B, wherein R$^1$ is cyclopropyl or phenyl substituted with a halogen, methyl or methoxy radical in the para position and optionally with 1-2 radicals selected from halogen and methyl in other positions; and R$^4$ is —N(R$^{24}$)R$^{25}$;

E) a compound according to D, wherein R$^2$ is CO$_2$R$^{12}$, CH$_2$OR$^{13}$, CHO or CH$_2$CO$_2$R$^{17}$;

F) a compound according to E, wherein R$^{24}$ is H, C(O)R$^{33}$ or C$_1$-C$_4$ alkyl optionally substituted with R$^{30}$; R$^{25}$ is H or C$_1$-C$_2$ alkyl; or R$^{24}$ and R$^{25}$ are taken together as =C(R$^{39}$)N(R$^{40}$)R$^{41}$;

G) a compound according to F, wherein R$^2$ is CO$_2$R$^{12}$; and R$^{24}$ and R$^{25}$ are H;

H) a compound according to G, wherein R$^{12}$ is H, C$_1$-C$_1$ alkyl or benzyl; or I) a compound according to A, wherein said compound is selected from the group consisting of:

methyl 6-amino-5-bromo-2-cyclopropyl-4-pyrimidinecarboxylate, ethyl 6-amino-5-bromo-2-cyclopropyl-4-pyrimidinecarboxylate, phenylmethyl 6-amino-5-bromo-2-cyclopropyl-4-pyrimidinecarboxylate, 6-amino-5-bromo-2-cyclopropyl-4-pyrimidinecarboxylic acid monosodium salt, methyl 6-amino-5-chloro-2-cyclopropyl-4-pyrimidinecarboxylate, phenylmethyl 6-amino-5-chloro-2-cyclopropyl-4-pyrimidinecarboxylate, 6-amino-5-chloro-2-cyclopropyl-4-pyrimidinecarboxylic acid monosodium salt, ethyl 6-amino-5-chloro-2-cyclopropyl-4-pyrimidinecarboxylate, methyl 6-amino-5-chloro-2-(4-chlorophenyl)-4-pyrimidinecarboxylate, ethyl 6-amino-5-chloro-2-(4-chlorophenyl)-4-pyrimidinecarboxylate, 6-amino-5-chloro-2-(4-chlorophenyl)-4-pyrimidinecarboxylic acid, ethyl 6-amino-2-(4-bromophenyl)-5-chloro-4-pyrimidinecarboxylate, methyl 6-amino-2-(4-bromophenyl)-5-chloro-4-pyrimidinecarboxylate, and 6-amino-2-(4-bromophenyl)-5-chloro-4-pyrimidinecarboxylic acid.

DETAILED DESCRIPTION OF THE INVENTION

The development of a 2,4-D resistance gene and its incorporation into crop plants and ornamental plants provides excellent options for weed control, particularly where the gene conferring 2,4-D resistance in used in combination with other genes conferring resistance or tolerance to other herbicides. An additional benefit of the disclosed methyltrasferase is its ability to confer resistance to fungal pathogens in a plant expressing the gene.

Figure 1:
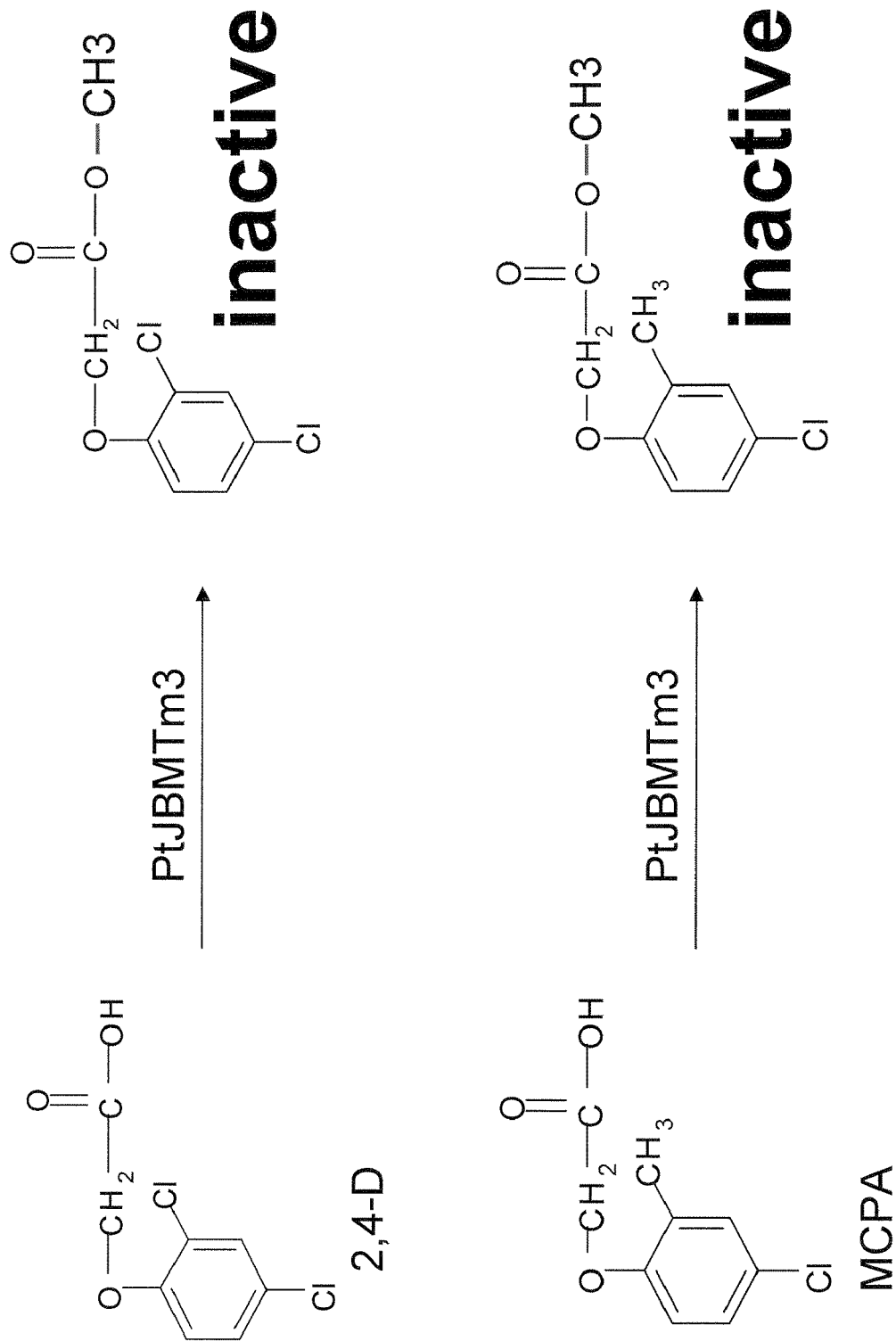
FIG. 1. Exemplary methylation of substrate by PtJBMTm3.
Figure 2:
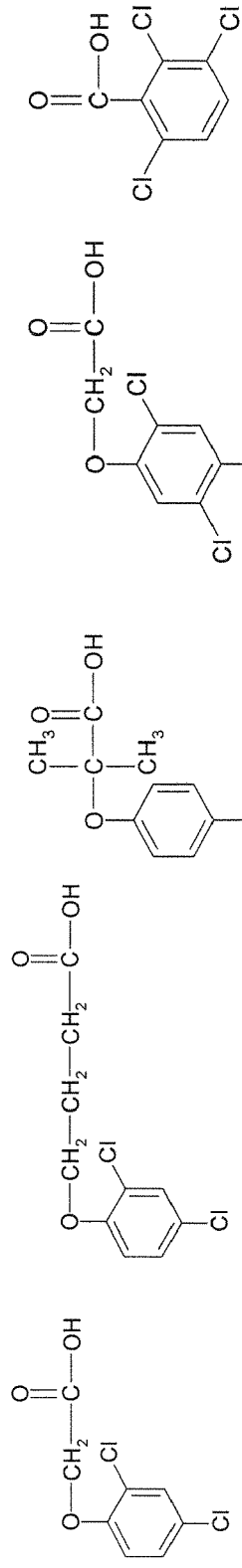
FIG. 2. Exemplary auxin-based herbicides and relative activity of PtJBMTm3 for the herbicide substrate (relative to ptJBMTm3 activity for 2,4-D as a substrate).
Figure 2:
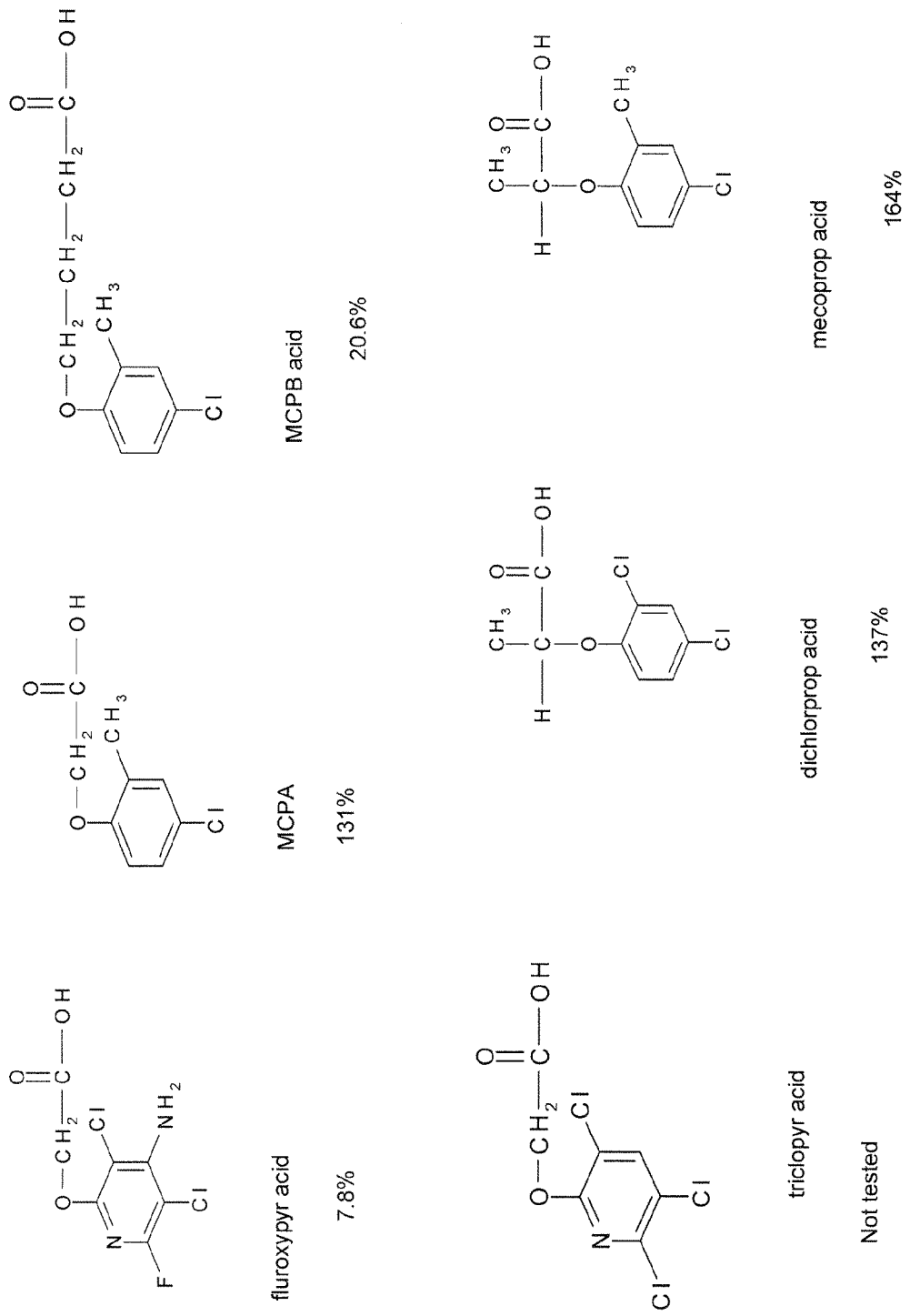
Figure 5:
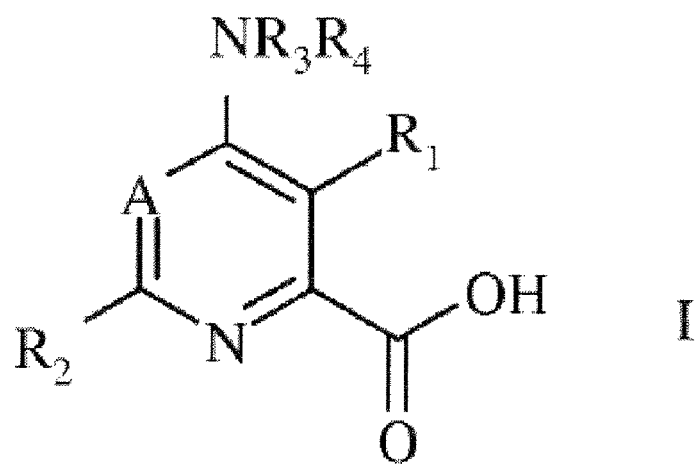
FIG. 5. Exemplary auxin-based herbicides disclosed in WO/2009/046090. The various substituents and compounds embraced by the structure are as follows.

A novel gene (PtJBMTm3) has now been identified which, when expressed in plants, allows the use of compositions comprising auxin-based herbicides in plants where inherent tolerance to auxin-based herbicides never existed. In plants that exhibit some degree of tolerance to auxin-based herbicides, this tolerance can be augmented by the introduction of PtJBMTm3 and expression of PtJBMTm3 in cells of the plant. Plants containing PtJBMTm3 alone now may be treated sequentially or with concomitantly with two, or more, auxin-based herbicidal compositions and such plants would be at reduced risk of injury from these herbicides. Non-limiting examples of auxin-based herbicides are found in Table 1, Table 2, FIG. 2 and FIGS. 4-6. Additional non-limiting examples of auxin-based herbicides include aminocyclopyrachlor, quinmerac and auxin-based herbicides disclosed in WO/2009/046090 (see FIG. 5) and WO/2005/063721 (see FIG. 6), the disclosures of which are hereby incorporated by reference in their entireties. As is apparent to those skilled in the art, numerous auxin-based herbicides are known. These herbicides are, typically, provided in the form of agriculturally acceptable salts (e.g., potassium, sodium) and/or esters (e.g., methyl esters, ethyl ester, isooctyl ester, methylheptyl ester, ethylhexyl ester, etc.). Thus, plants comprising PtJBMTm3 will exhibit some degree to tolerance to such herbicides and can be treated with such herbicides without incurring significant damage.

Additionally, PtJBMTm3 can provide protection in planta to fungal pathogens when expressed within a plant cell. Thus, a method of increasing a plant's resistance to fungal pathogens is provided that comprises expressing the gene product of PtJBMTm3 in a plant or plant cell in amounts sufficient to confer resistance to said fungal pathogen. In this aspect of the invention, an increase in resistance to a fungal pathogen is measured against a control plant that has not been transformed with PtJBMTm3 or that has been transformed with another gene (that does not confer resistance to a fungal pathogen) as a control, Non-limiting examples of fungal pathogens that may be controlled include Asian soybean rust, *cercospora* of soybean and gray leaf spot in corn.

Another aspect of the invention provides for combining PtJBMTm3 with a glyphosate tolerance trait (and/or with other herbicide-tolerance traits) within a transgenic plant. Thus, one can use glyphosate and auxin-based (e.g., 2,4-D) herbicides on the same crop/plant. As would be apparent to one skilled in the art, such herbicides could be simultaneously applied in a tank mixture comprising two or more herbicides (e.g., glyphosate and 2,4-D). Alternatively, individual/sequential application of single herbicide compositions can be performed as pre-plant, preemergence, postemergence-directed, layby or postemergence weed control. The individual/sequential application of these herbicide compositions can be separated by a period of time ranging from approximately 2 hours to approximately 3 months.

As discussed above, one or more genes conferring resistance or tolerance to additional herbicides can be introduced into a plant or plant cell. For example, genes conferring: glyphosate resistance (e.g., resistant plant or bacterial EPSPS); glyphosate oxidoreductase (e.g., GOX or GAT); glufosinate resistance (e.g., Pat or bar); resistance to herbicides that inhibit acetolactate synthase (ALS) (e.g., AHAS, Csr1 or SurA); bromoxynil resistance (e.g., Bxn); resistance to herbicide inhibitors of HPPD (4-hydroxlphenyl-pyruvate-dioxygenase); resistance to herbicide inhibitors of phytoene desaturase (PDS); resistance to photosystem II inhibiting herbicides (e.g., psbA); resistance to photosystem I inhibiting herbicides; resistance to protoporphyrinogen oxidase IX (PPO)-inhibiting herbicides (e.g., PPO-1); resistance to phenylurea herbicides (e.g., CYP76B1); resistance to dicamba-based herbicides (e.g., dicamba-degrading enzymes such as those disclosed in US 20030135879, which is hereby incorporated by reference in its entirety); resistance to auxin-based herbicides (e.g., AAD12 conferring resistance to phenoxy and pyridyloxy auxins); and ACCase inhibitors can be used to provide resistance to given herbicide.

Examples of herbicides to which resistance or tolerance can be conferred by the aforementioned genes include, and are not limited to: ALS inhibitors such as sulfonylureas (e.g., chlorimuron-ethyl, metsulfuron-methyl, rim sulfuron, thifensulfuron-methyl, tribenuron-methyl, chlorsulfuron, halosulfuron, nicosulfuron, sulfometuron, sulfosulfuron, trifloxysulfuron); imidazoloninones such as imazapyr, imazamox, imazethapyr or imazaquin); triazolopyrimidine sulfonanilides (such as cloransulam-methyl, diclosulam, florasulam, flumetsulam, metosulam, and penoxsulam), pyrimidinylthiobenzoates (such as bispyribac and pyrithiobac), and flucarbazone. Some examples of HPPD inhibiting herbicides include but are not limited to tembotrione, topramezone, mesotrione, isoxaflutole, and sulcotrione. PPO inhibiting herbicides include but are not limited to flumiclorac, flumioxazin, flufenpyr, pyraflufen, fluthiacet, butafenacil, carfentrazone, sulfentrazone, and the diphenylethers (such as acifluorfen, fomesafen, lactofen, and oxyfluorfen).

Not only can PtJBMTm3 can be used alone or in combination with genes conferring resistance to other herbicides, plants comprising PtJBMTm3 (alone or in combination with other genes conferring herbicide resistance) can be transformed with nucleic acids that provide additional traits (e.g., insect resistance, fungal resistance, or stress tolerance, increased yield, improved oil profile, and/or improved fiber quality).

Nucleic Acids and Polypeptides

As discussed above, the subject invention provides nucleic acids and polypeptides designated as PtJBMTm3 (SEQ ID NO: 1) and PtJBMTm3 (SEQ ID NO: 2), respectively. PtJBMTm3 has the ability to methylate auxin-based herbicides. Additionally, PtJBMTm3 can also confer resistance to various fungal pathogens when expressed with in a plant cell. Thus, the subject invention also provides a method for the methylation of 2,4-dichlorophenoxyacetic acid (2,4-D) and other auxin-based herbicides in plants and/or in vitro comprising contacting an auxin-based herbicide with a polypeptide comprising SEQ ID NO: 2 under conditions allowing for the methylation of the auxin-based herbicide (e.g., in the presence of a cofactor such as S-adenosyl methionine (SAM)).

Accordingly, one aspect of the invention provides a polypeptide comprising SEQ ID NO: 2 (PtJBMTm3). In the context of the instant invention, the terms "oligopeptide", "polypeptide", "peptide" and "protein" can be used interchangeably; however, it should be understood that the invention does not relate to the polypeptides in natural form, that is to say that they are not in their natural environment but that the polypeptides may have been isolated or obtained by purification from natural sources or obtained from host cells prepared by genetic manipulation (e.g., the polypeptides, or fragments thereof, are recombinantly produced by host cells or by chemical synthesis and, optionally, purified from the host cell or reaction mixture). The terms "oligopeptide", "polypeptide", "peptide" and "protein" are also used, in the instant specification, to designate a series of residues, typically L-amino acids, connected one to the other, typically by peptide bonds between the α-amino and carboxyl groups of adjacent amino acids. The subject invention also provides polypeptides comprising SEQ ID NO: 2 and/or polypeptide fragments of SEQ ID NO: 2, wherein said fragments have the ability to methylate auxin-based herbicide substrates or confer resistance to fungal pathogens or auxin-based herbicides when expressed in a plant.

Polypeptide fragments according to the subject invention, usually comprise a contiguous span of at least 3, 4, 5, 6, 7, 8, 9, 10, 11, 12, 13, 14, 15, 16, 17, 18, 19, 20, 21 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363 or 364 consecutive amino acids of SEQ ID NO:2. Certain embodiments provide fragments of SEQ ID NO: 2 in which amino acids are deleted from the C-terminus, N-terminus or both the C-terminus and N-terminus of the polypeptide, provided that active site residues are not deleted (see FIG. 3). Any fragment of SEQ ID NO: 2 disclosed herein retains the biological activity of methylating auxin-based herbicide substrates and/or the ability to confer resistance to fungal pathogens or auxin-based herbicides when expressed in a plant.

Fragments, as described herein, can be obtained by cleaving the polypeptides of the invention with a proteolytic enzyme (such as trypsin, chymotrypsin, or collagenase) or with a chemical reagent, such as cyanogen bromide (CNBr). Alternatively, polypeptide fragments can be generated in a highly acidic environment, for example at pH 2.5. Such polypeptide fragments may be equally well prepared by chemical synthesis or using hosts transformed with an expression vector according to the invention. The transformed host cells contain a nucleic acid, allowing the expression of these fragments, under the control of appropriate elements for regulation and/or expression of the polypeptide fragments.

A "variant polypeptide" (or polypeptide variant) is to be understood to designate polypeptides exhibiting, in relation to the natural polypeptide, certain modifications. These modifications can include a deletion, addition, or substitution of at least one amino acid, a truncation, an extension, a chimeric fusion, a mutation, or polypeptides exhibiting post-translational modifications. Among these homologous variant polypeptides, are those comprising amino acid sequences exhibiting between at least (or at least about) 20.00% to 99.99% (inclusive) identity to the full length polypeptide (SEQ ID NO: 2) are another aspect of the invention. The aforementioned range of percent identity is to be taken as including, and providing written description and support for, any fractional percentage, in intervals of 0.01%, between 20.00% and, up to, including 99.99%. These percentages are purely statistical and differences between two polypeptide sequences can be distributed randomly and over the entire sequence length. Thus, variant polypeptides can have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity with the polypeptide sequences of the instant invention. In a preferred embodiment, a variant or modified polypeptide exhibits at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity to SEQ ID NO: 2. Typically, the percent identity is calculated with reference to the full-length, native, and/or naturally occurring polypeptide (e.g., SEQ ID NO: 2). In all instances, variant polypeptides retain at least one of the activities associated with the polypeptide set forth in SEQ ID NOs: 2, particularly the ability to methylate an auxin-based substrate, confer resistance to an auxin-based herbicide when expressed in a plant or confer resistance to fungal pathogens when expressed in a plant.

In some embodiments, variant polypeptides contain no amino acid substitutions in the active site residues identified in FIG. 3 and amino acid substitutions can be made in various other amino acids. In other embodiments, amino acid substitutions can be made in active site residues. In other embodiments, variants in which several, i.e. between 5 and 10, 1 and 5, 1 and 3, 1 and 2 or just 1 amino acid(s) are substituted, deleted or added in any combination are provided. Especially preferred are silent substitutions, additions and deletions, which do not alter the properties and activities of the protein (i.e., the ability to methylate an auxin-based substrate (herbicide), confer resistance in a plant to an auxin-based herbicide and/or confer resistance to fungal pathogens when expressed in a plant). Examples of suitable amino acid substitutions are provided below. For example, amino acids within the groups provided below may be substituted for each other. Alternatively, conservative/synonymous amino acids may be substituted for a given amino acid as illustrated in Table 3. In all instances, variant polypeptides retain at least one of the activities associated with the polypeptide set forth in SEQ ID NOs: 2, particularly the ability to methylate an auxin-based substrate, confer resistance to an auxin-based herbicide when expressed in a plant and/or confer resistance to fungal pathogens when expressed in a plant. Any amino acid substitution should be a "conservative", "synonymous" or "safe" substitution, which is commonly defined a substitution introducing an amino acids having sufficiently similar chemical properties (e.g. a basic, positively charged amino acid should be replaced by another basic, positively charged amino acid), in order to preserve the structure and the biological function of the molecule. Examples of such "conservative", "synonymous" or "safe" substitutions are provided in Table 3 and the literature provides many models on which the selection of conservative amino acids substitutions can be performed on the basis of statistical and physico-chemical studies on the sequence and/or the structure of proteins (Rogov S. I. and Nekrasov A. N., 2001). Protein design experiments have shown that the use of specific subsets of amino acids can produce foldable and active proteins, helping in the classification of amino acid "synonymous" substitutions which can be more easily accommodated in protein structure, and which can be used to detect functional and structural homologs and paralogs (Murphy L. R. et al., 2000). The groups of synonymous and preferred synonymous amino acids are shown in Table 3. Alternatively, the application provides embodiments in which amino acids residues within each of the following groups can be substituted for each other: (i) Ala, Val, Leu and Ile; (ii) Ser and Thr; (iii) Asp and Glu; (iv) Asn and Gln; (v) Lys and Arg; or (vi) Phe and Tyr. In all instances, variant polypeptides retain at least one of the activities associated with the polypeptide set forth in SEQ ID NOs: 2, particularly the ability to methylate an auxin-based substrate or confer resistance to fungal pathogens or auxin-based herbicides when expressed in a plant.

In another aspect of the invention, polypeptides can also comprise one or more heterologous polypeptide sequences (e.g., tags that facilitate purification of the polypeptides of the invention (see, for example, U.S. Pat. No. 6,342,362, hereby incorporated by reference in its entirety; Altendorf et al., 1999-WWW, 2000; Baneyx 1999; Eihauer et al., 2001; Jones et al., 1995; Margolin 2000; Puig et al., 2001; Sassenfeld 1990; Sheibani 1999; Skerra et al., 1999; Smith 1998; Smyth et al., 2000; Unger 1997, each of which is hereby incorporated by reference in their entireties), or commercially available tags from vendors such as such as STRATAGENE (La Jolla, Calif.), NOVAGEN (Madison, Wis.), QIAGEN, Inc., (Valencia, Calif.), or InVitrogen (San Diego, Calif.).

Yet another aspect of the invention provides:

a) a polynucleotide sequence encoding a polypeptide comprising SEQ ID NO: 2 or encoding one or a polynucleotide encoding a polypeptide fragment of SEQ ID NO: 2;

b) a polynucleotide sequence that is at least 70% identical to SEQ ID NO: 1 and encodes a polypeptide having methyltransferase activity or a polynucleotide that comprises SEQ ID NO: 1;

c) a polynucleotide sequence at least 8 consecutive nucleotides of a polynucleotide sequence as set forth in (a) or (b);

d) a polynucleotide that is complementary to the polynucleotides set forth in (a), (b) or (c);

e) a polynucleotide that hybridizes under low, intermediate or high stringency with a polynucleotide sequence as set forth in (a), (b), (c) or (d);

f) a genetic construct comprising a polynucleotide sequence as set forth in (a), (b), (c), (d) or (e);

g) a vector comprising a polynucleotide or genetic construct as set forth in (a), (b), (c), (d), (e) or (f);

h) a host cell comprising a vector as set forth in (g), a genetic construct as set forth in (f), or a polynucleotide as set forth in any one of (a), (b), (c), (d) or (e); or i) a transgenic plant, plant cell, or plant part comprising a vector as set forth in (g), a genetic construct as set forth in (f) or a polynucleotide as set forth in any one of (a), (b), (c), (d) or (e).

Genetic constructs of the subject invention can also contain additional regulatory elements such as promoters and enhancers and, optionally, selectable markers. Also within the scope of the subject instant invention are vectors or expression cassettes containing genetic constructs as set forth herein or polynucleotides encoding the polypeptides, set forth supra, operably linked to regulatory elements (e.g., promoters or enhancers). The vectors and expression cassettes may contain additional transcriptional control sequences as well. The vectors and expression cassettes may further comprise selectable markers. The expression cassette may contain at least one additional gene, operably linked to control elements, to be co-transformed into the organism. Alternatively, the additional gene(s) and control element(s) can be provided on multiple expression cassettes. Such expression cassettes are provided with a plurality of restriction sites for insertion of the sequences of the invention to be under the transcriptional regulation of the regulatory regions. The expression cassette(s) may additionally contain selectable marker genes operably linked to control elements.

The expression cassette will include in the 5'-3' direction of transcription, a transcriptional and translational initiation region, a DNA sequence of the invention, and transcriptional and translational termination regions. The transcriptional initiation region, the promoter, may be native (analogous) or foreign (heterologous) to the host cell. Additionally, the promoter may be the natural sequence or alternatively a synthetic sequence. By "foreign" is intended that the transcriptional initiation region/promoter is not found in the native plant into which the transcriptional initiation region is introduced. As used herein, a chimeric gene comprises a coding sequence operably linked to a transcriptional initiation region that is heterologous to the coding sequence.

Another aspect of the invention provides vectors for the cloning and/or the expression of a polynucleotide sequence taught herein. Vectors of this invention can also comprise elements necessary to allow the expression and/or the secretion of the said nucleotide sequences in a given host cell. The vector can contain a promoter, signals for initiation and for termination of translation, as well as appropriate regions for regulation of transcription. In certain embodiments, the vectors can be stably maintained in the host cell and can, optionally, contain signal sequences directing the secretion of translated protein. These different elements are chosen according to the host cell used. Vectors can integrate into the host genome or, optionally, be autonomously-replicating vectors.

The subject invention also provides for the expression of a polypeptide or peptide fragment encoded by a polynucleotide sequence disclosed herein comprising the culture of a host cell transformed with a polynucleotide of the subject invention under conditions that allow for the expression of the polypeptide and, optionally, recovering the expressed polypeptide.

The disclosed polynucleotide sequences can also be regulated by a nucleic acid sequence so that the protein or peptide is expressed in a host transformed with the recombinant DNA molecule. For example, expression of a protein or peptide may be controlled by any promoter/enhancer element known in the art. Promoters which may be used to control expression include, but are not limited to, the CMV-IE promoter, the SV40 early promoter region (Benoist and Chambon 1981), the promoter contained in the 3' long terminal repeat of Rous sarcoma virus (Yamamoto et al., 1980), the herpes simplex thymidine kinase promoter (Wagner et al., 1981), the regulatory sequences of the metallothionein gene (Brinster et al., 1982); prokaryotic vectors containing promoters such as the β-lactamase promoter (VIIIa-Kamaroff et al., 1978), or the tac promoter (deBoer et al., 1983); see also "Useful proteins from recombinant bacteria" in Scientific American, 1980, 242:74-94; plant expression vectors comprising the nopaline synthetase promoter region (Herrera-Estrella et al., 1983) or the cauliflower mosaic virus 35S RNA promoter (Gardner et al., 1981), and the promoter of the photosynthetic enzyme ribulose biphosphate carboxylase (Herrera-Estrella et al., 1984); promoter elements from yeast or fungi such as the Gal 4 promoter, the ADC (alcohol dehydrogenase) promoter, PGK (phosphoglycerol kinase) promoter, and/or the alkaline phosphatase promoter. Other suitable promoters include cassaya vein mosaic virus promoter, CaMV 35S promoter, Figwort Mosaic Virus promoter, rice actin promoter (or other plant derived actin promoters), phaseolin promoter, *Arabidopsis thaliana* Ubiquitin 10 promoter, maize ubiquitin promoter, *Arabidopsis thaliana* Act2 promoter, *Arabidopsis thaliana* Ubiquitin 11 promoter, and *Arabidopsis thaliana* Ubiquitin 3 promoter.

The invention also encompasses the host cells transformed by a vector according to the invention. These cells may be obtained by introducing into host cells a nucleotide sequence inserted into a vector as defined above, and then culturing the said cells under conditions allowing the replication and/or the expression of the polynucleotide sequences of the subject invention.

The host cell may be chosen from eukaryotic or prokaryotic systems, such as for example bacterial cells, (Gram negative or Gram positive), yeast cells (for example, *Saccharomyces cereviseae* or *Pichia pastoris*), animal cells (such as Chinese hamster ovary (CHO) cells), plant cells, and/or insect cells using baculovirus vectors. In some embodiments, the host cells for expression of the polypeptides include, and are not limited to, those taught in U.S. Pat. Nos. 6,319,691, 6,277,375, 5,643,570, or 5,565,335, each of which is incorporated by reference in its entirety, including all references cited within each respective patent.

Furthermore, a host cell may be chosen which modulates the expression of the inserted sequences, or modifies and processes the gene product in the specific fashion desired. Expression from certain promoters can be elevated in the presence of certain inducers; thus, expression of the genetically engineered polypeptide may be controlled. Furthermore, different host cells have characteristic and specific mechanisms for the translational and post-translational processing and modification (e.g., glycosylation, phosphorylation) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in plant cells can be used to ensure "native" glycosylation of a plant-derived protein. Furthermore, different vector/host expression systems may effect processing reactions to different extents.

Also provided are transformed plant cells, transgenic seeds, transgenic plant parts and transgenic plants which contain one or more polynucleotide sequence, genetic construct, vector, or expression cassette comprising one or more of the polynucleotides disclosed herein, or biologically active fragments thereof, operably linked to control elements. As used herein, the term "plant" includes algae and higher plants (including, but not limited to trees). Thus, algae, monocots, and dicots may be transformed with genetic constructs of the invention, expression cassettes, or vectors according to the invention.

Transgenic plant is herein defined as a plant cell culture, plant cell line, plant tissue culture, lower plant, monocot plant, dicot plant, or progeny or part thereof derived from a transformed plant cell or protoplast, wherein the genome of the transformed plant contains foreign DNA, introduced by laboratory techniques, not originally present in a native, non-transgenic plant cell of the same species. The terms "transgenic plant" and "transformed plant" have sometimes been used in the art as synonymous terms to define a plant whose DNA contains an exogenous DNA molecule. Where appropriate, the polynucleotides encoding the polypeptides set forth herein can be optimized for expression in the transformed plants, plant cells or plant parts. That is, the genes can be synthesized using species-preferred codons corresponding to the plant species of interest. Methods are available in the art for synthesizing for example, plant-preferred genes. See, for example, U.S. Pat. Nos. 5,380,831 and 5,436,391 or Murray et al. (1989), each of which is incorporated by reference in its entirety.

Construction of gene cassettes for expressing polypeptides in plants is readily accomplished utilizing well known methods, such as those disclosed in Sambrook et al. (1989); and Ausubel, M. et al. (1987). In preparing the constructs of this invention, the various DNA fragments may be manipulated, so as to provide for the DNA sequences in the proper orientation and, as appropriate, in the proper reading frame. Adapters or linkers may be employed for joining the DNA fragments or other manipulations may be involved to provide for convenient restriction sites, removal of superfluous DNA, removal of restriction sites, or the like.

In carrying out the various steps, cloning is employed, so as to amplify a vector containing the promoter/gene of interest for subsequent introduction into the desired host cells. A wide variety of cloning vectors are available, where the cloning vector includes a replication system functional in *Escherichia coli* (*E. coli*) and a marker which allows for selection of the transformed cells. Illustrative vectors include pBR322, pUC series, pACYC184, Bluescript series (Stratagene) etc. Thus, the sequence may be inserted into the vector at an appropriate restriction site(s), the resulting plasmid used to transform the *E. coli* host (e.g., *E. coli* strains HB101, JM101 and DH5α), the *E. coli* grown in an appropriate nutrient medium and the cells harvested and lysed and the plasmid recovered. Analysis may involve sequence analysis, restriction analysis, electrophoresis, or the like. After each manipulation, the DNA sequence to be used in the final construct may be restricted and joined to the next sequence, where each of the partial constructs may be cloned in the same or different plasmids.

Vectors are available or can be readily prepared for transformation of plant cells. In general, plasmid or viral vectors should contain all the DNA control sequences necessary for both maintenance and expression of a heterologous DNA sequence in a given host. Such control sequences generally include a leader sequence and a DNA sequence coding for translation start-signal codon, a translation terminator codon, and a DNA sequence coding for a 3' UTR signal controlling messenger RNA processing. Selection of appropriate elements to optimize expression in any particular species is a matter of ordinary skill in the art utilizing the teachings of this disclosure. Finally, the vectors should desirably have a marker gene that is capable of providing a phenotypical property which allows for identification of host cells containing the vector.

The present invention is not limited to any particular method for transforming plant cells. Technology for introducing DNA into plant cells is well-known to those of skill in the art. Four basic methods for delivering foreign DNA into plant cells have been described. Chemical methods (Graham and van der Eb, 1973; Zatloukal et al., 1992); physical methods including microinjection (Capecchi, 1980), electroporation (Wong and Neumann 1982; Fromm et al., 1985; U.S. Pat. No. 5,384,253) and the gene gun (Johnston and Tang, 1994; Fynan et al., 1993); viral methods (Clapp, 1993; Lu et al., 1993; Eglitis and Anderson 1988; Eglitis et al., 1988); and receptor-mediated methods (Curiel et al., 1991; Curiel et al., 1992; Wagner et al., 1992).

The introduction of DNA into plant cells by means of electroporation is well-known to those of skill in the art. Plant cell wall-degrading enzymes, such as pectin-degrading enzymes, are used to render the recipient cells more susceptible to transformation by electroporation than untreated cells. To effect transformation by electroporation one may employ either friable tissues such as a suspension culture of cells, or embryogenic callus, or immature embryos or other organized tissues directly. It is generally necessary to partially degrade the cell walls of the target plant material with pectin-degrading enzymes or mechanically wounding in a controlled manner. Such treated plant material is ready to receive foreign DNA by electroporation.

Another method for delivering foreign transforming DNA to plant cells is by microprojectile bombardment. In this method, microparticles are coated with foreign DNA and delivered into cells by a propelling force. Such micro particles are typically made of tungsten, gold, platinum, and similar metals. An advantage of microprojectile bombardment is that neither the isolation of protoplasts (Cristou et al., 1988) nor the susceptibility to *Agrobacterium* infection is required. An illustrative embodiment of a method for delivering DNA into maize cells by acceleration is a Biolistics Particle Delivery System, which can be used to propel particles coated with DNA or cells through a screen onto a filter surface covered with corn cells cultured in suspension. The screen disperses the particles so that they are not delivered to the recipient cells in large aggregates. For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids.

*Agrobacterium*-mediated transfer is a widely applicable system for introducing foreign DNA into plant cells because the DNA can be introduced into whole plant tissues, eliminating the need to regenerate an intact plant from a protoplast. The use of *Agrobacterium*-mediated plant integrating vectors to introduce DNA into plant cells is well known in the art. See, for example, the methods described in Fraley et al. (1985) and Rogers et al. (1987). Further, the integration of the Ti-DNA is a relatively precise process resulting in few rearrangements. The region of DNA to be transferred is defined by the border sequences, and intervening DNA is usually inserted into the plant genome as described in Spielmann et al. (1986) and Jorgensen et al. (1987).

*Agrobacterium* transformation vectors are capable of replication in *E. coli* as well as *Agrobacterium*, allowing for convenient manipulations. Moreover, recent technological advances in vectors for *Agrobacterium*-mediated gene transfer have improved the arrangement of genes and restriction sites in the vectors to facilitate construction of vectors capable of expressing various proteins or polypeptides. Convenient multi-linker regions flanked by a promoter and a polyadenylation site for direct expression of inserted polypeptide coding genes are suitable for present purposes. In addition, *Agrobacterium* containing both armed and disarmed Ti genes can be used for the transformations.

Transformation of plant protoplasts can be achieved using methods based on calcium phosphate precipitation, polyethylene glycol treatment, electroporation, and combinations of these treatments (see, e.g., Potrykus et al., 1985; Marcotte et al., 1988). Application of these systems to different plant species depends on the ability to regenerate the particular species from protoplasts.

The introduction of nucleic acids encoding PtJBMTm3 into a plant or plant cell, and its subsequent expression, provides tolerance to combinations of herbicides that would control many broadleaf weeds. PtJBMTm3 can serve as an excellent herbicide tolerant crop (HTC) trait to combine with other HTC traits [e.g., glyphosate resistance, glufosinate resistance, ALS-inhibitor (e.g., imidazolinone, sulfonylurea, triazolopyrimidine sulfonanilide) resistance, bromoxynil resistance, HPPD-inhibitor resistance, PPO-inhibitor resistance, et al.], and/or insect resistance traits (Cry1F, Cry1Ab, Cry 34/45, other Bt. Proteins, or insecticidal proteins of a non-Bacillis origin), for example. Additionally, PtJBMTm3 also be used as a selectable marker to aid in selection of primary transformants of plants genetically engineered with a second gene or group of genes.

This invention can be applied in the context of commercializing a 2,4-D resistance trait in combination with currently available glyphosate resistant soybeans, for example. Soybeans are one example of a preferred crop for transformation according to the subject invention. However, this invention can be utilized in other monocots (such as pasture grasses or turf grass to increase resistance to auxin-based herbicides) and dicot crops like alfalfa, clover or various tree species. Likewise, 2,4-D tolerance, or tolerance to other auxin-based herbicides can be increased in grass crops where tolerance to auxin-based herbicides is already present, albeit at lower levels. Increased tolerance to auxin-based herbicides can provide growers the opportunity to use these herbicides at higher rates and over a wider application timing without the risk of significant plant injury. PtJBMTm3 expression in plants can also be used as a selectable marker Plants producing PtJBMTm3 proteins will preferably produce sufficient amounts of protein that will render the plant completely or partially resistant or tolerant to an auxin-based herbicide (at a typical application rate for the herbicide; typical application rates can be found in the well-known *Herbicide Handbook* (Weed Science Society of America, Eighth Edition, 2002), for example). As used herein unless otherwise indicated, herbicide "resistance" is heritable and allows a plant to grow and reproduce in the presence of a typical herbicidally effective treatment by an herbicide for a given plant, as suggested by the current edition of *The Herbicide Handbook* in print at the time of the filing of the subject disclosure. As is recognized by those skilled in the art, a plant may still be considered "resistant" even though some degree of plant injury from herbicidal exposure is apparent. As used herein, the terms "tolerance" and "resistance," relate to the improved capacity of a particular plant to withstand the various degrees of herbicide induced injury when compared to wild-type plants (i.e., plants of the same genus and species that have not been transformed with PtJBMTm3) treated at the same herbicide dose.

As discussed above, PtJBMTm3 can be introduced into a wide variety of plant hosts. Preferred plants (and plant cells) are corn, *Arabidopsis*, tobacco, soybeans, cotton, canola, rice, cereals (e.g., wheat, barley, oats, rye, triticale, etc.), turf, legume forages (e.g., alfalfa and clover), pasture grasses, *populus* trees, switchgrass (or other biofuels) and the like. Other types of transgenic plants can also be made according to the subject invention, such as fruits, vegetables, ornamental plants, and trees. More generally, dicots and/or monocots can be used in various aspects of the subject invention (e.g., increasing resistance to fungal pathogens and/or resistance to auxin-based herbicides.

Plant cells transfected with a polynucleotide of the subject invention can be regenerated into whole plants. The subject invention includes cell cultures including tissue cell cultures, liquid cultures, and plated cultures. Seeds produced by and/or used to generate plants of the subject invention are also included within the scope of the subject invention. Other plant tissues and parts are also included in the subject invention. The subject invention likewise includes methods of producing plants or cells comprising a polynucleotide of the subject invention. One preferred method of producing such plants is by planting a seed of the subject invention.

Some other aspects of the invention provide for the use of safeners and/or plant activators to further protect plants and/or to add cross resistance to more herbicides. Safeners typically act to increase plants immune system by activating/expressing cP450. Herbicide safeners include benoxacor, cloquintocet, cyometrinil, dichlormid, dicyclonon, diethotate, fenchlorazole, fenclorim, flurazole, fluxofenim, furilazole, isoxadifen, mefenpyr, mephenate, naphthalic anhydride, and oxabetrinil.

Unless specifically indicated or implied, the terms "a", "an", and "the" signify "at least one" as used herein. Additionally, the terms "comprising", "consisting essentially of", and "consisting of" can be used interchangeably throughout the subject specification.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLES

Example 1

Biochemical Assays to Determine Detoxification Activity

The detoxification activity of PtJBMTm3 was determined using radiochemical methyltransferase assays. The assays were performed with a 50 μL volume containing 50 mM Tris-HCl, pH 7.5, 1 mM of individual auxin mimic herbicides dissolved in water, and 3 μM $^{14}$C—S-Adenosyl methionine (SAM) with a specific activity of 51.4 mCi/mmol (Perkin Elmer, Boston, Mass.). The assay was initiated by addition of SAM, maintained at 25° C. for 30 min, and stopped by addition of ethyl acetate (150 μL). After phase separation by one min centrifugation at 14,000 g, the upper organic phase was counted using a liquid scintillation counter (Beckman Coulter, Fullerton, Calif.) as previously described (D'Auria et al., 2002). Radioactivity counts in the organic phase indicated the amount of synthesized methyl esters, which are the detoxificated products of individual auxin mimic herbicides. The relative assay activities of PtJBMT and PtJBMTm3 with auxin-based herbicides is illustrated in Table 2 (the activity of PtJBMTm3 with jasmonic acid was set as 1).

TABLE 1

Exemplary commercially available auxin-based herbicides. Possible use rate ranges can be as stand-alone treatments or in combination with other herbicides in both crop and non-crop uses.

| Chemical name | CAS No. | Possible use rate ranges (g ae/ha) | Preferred use rate ranges (g ae/ha) | Structure |
|---|---|---|---|---|
| 2,4-D | 94-75-7 | 25-4000 | 280-1120 | 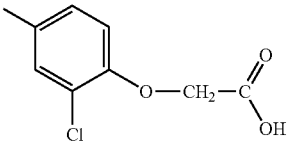 |
| 2,4,5-T | 93-76-5 | 25-4000 | 25-4000 | 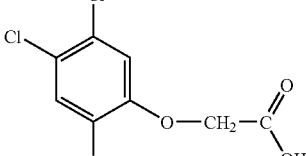 |
| 4-CPA | 122-88-3 | 25-4000 | 25-4000 | 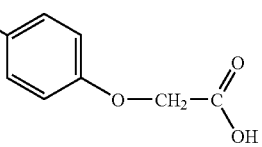 |
| 3,4-DA | 588-22-7 | 25-4000 | 25-4000 | 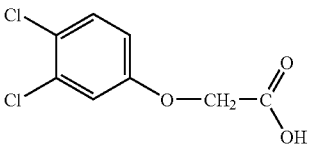 [SMILES: O=C(O)COc1ccc(Cl)c(Cl)c1] |
| MCPA | 94-74-6 | 25-4000 | 125-1550 | 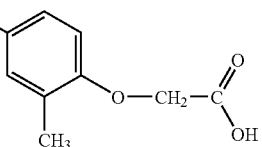 |
| Triclopyr | 55335-06-3 | 50-2000 | 70-840 | 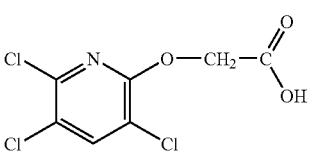 [SMILES: O=C(O)COc1nc(Cl)c(Cl)cc1Cl] |

TABLE 1-continued

Exemplary commercially available auxin-based herbicides. Possible use rate ranges can be as stand-alone treatments or in combination with other herbicides in both crop and non-crop uses.

| Chemical name | CAS No. | Possible use rate ranges (g ae/ha) | Preferred use rate ranges (g ae/ha) | Structure |
|---|---|---|---|---|
| Fluroxypyr | 69377-81-7 | 25-2000 | 35-560 | (structure shown) |

TABLE 2

Relative assay activities of PtJBMT and PtJBMTm3 with auxin-based herbicides (the activity of PtJBMTm3 with jasmonic acid was set as 1).

|  | PtJBMT | PtJBMT M3 |
|---|---|---|
| Jasmonic acid | 85.1% | 1 |
| 4-Cl-IAA | 1.1% | 33.6% |
| IBA | 0.8% | 30.3% |
| NAA | 7.8% | 91.8% |
| PAA | 0.8% | 58.3% |
| 2,4-D | 1.7% | 57.5% |
| 2,4-DB | 0.5% | 38.7% |
| PCIB | 8.0% | 96.9% |
| 2,4,5-T | 0.4% | 25.5% |
| 2,3,6 Trichlorobenzoic acid | 15.0% | 75.4% |
| quinclorac | 11.2% | 91.3% |
| dicamba | 2.3% | 73.9% |
| picloram | 3.7% | 78.1% |
| clopyralid | 17.1% | 94.1% |
| fluroxypyr | 0.6% | 4.2% |
| MCPA | 3.5% | 70.0% |
| MCPB | 0.1% | 11.0% |
| dichlorprop | 7.3% | 73.0% |
| mecoprop | 12.8% | 87.5% |

TABLE 3

Amino Acid Substitution Table

| Amino Acid | Conservative/ Synonymous Amino Acids | Preferred Conservative/ Synonymous Amino Acids |
|---|---|---|
| Ser | Gly, Ala, Ser, Thr, Pro | Thr, Ser |
| Arg | Asn, Lys, Gln, Arg, His | Arg, Lys, His |
| Leu | Phe, Ile, Val, Leu, Met | Ile, Val, Leu, Met |
| Pro | Gly, Ala, Ser, Thr, Pro | Pro |
| Thr | Gly, Ala, Ser, Thr, Pro | Thr, Ser |
| Ala | Gly, Thr, Pro, Ala, Ser | Gly, Ala |
| Val | Met, Phe, Ile, Leu, Val | Met, Ile, Val, Leu |
| Gly | Ala, Thr, Pro, Ser, Gly | Gly, Ala |
| Ile | Phe, Ile, Val, Leu, Met | Ile, Val, Leu, Met |
| Phe | Trp, Phe, Tyr | Tyr, Phe |
| Tyr | Trp, Phe, Tyr | Phe, Tyr |
| Cys | Ser, Thr, Cys | Cys |
| His | Asn, Lys, Gln, Arg, His | Arg, Lys, His |
| Gln | Glu, Asn, Asp, Gln | Asn, Gln |
| Asn | Glu, Asn, Asp, Gln | Asn, Gln |
| Lys | Asn, Lys, Gln, Arg, His | Arg, Lys, His |
| Asp | Glu, Asn, Asp, Gln | Asp, Glu |
| Glu | Glu, Asn, Asp, Gln | Asp, Glu |
| Met | Phe, Ile, Val, Leu, Met | Ile, Val, Leu, Met |
| Trp | Trp, Phe, Tyr | Trp |

References

U.S. Pat. No. 5,384,253
U.S. Pat. No. 5,380,831
U.S. Pat. No. 5,436,391
U.S. Pat. No. 6,319,691
U.S. Pat. No. 6,277,375
U.S. Pat. No. 5,643,570
U.S. Pat. No. 5,565,335
U.S. Pat. No. 6,342,362
U.S. Published Application No. 20030135879
Altendorf, K. et al. (1999-WWW, 2000) "Structure and Function of the $F_o$ Complex of the ATP Synthase from *Escherichia Coli*" *J. of Experimental Biology* 203:19-28.
Ausubel, M. et al. (1987) Current Protocols in Molecular Biology, John Wiley and Sons, New York, N.Y.
Baneyx, F. (1999) "Recombinant Protein Expression in *Escherichia coli*" *Biotechnology* 10:411-21.
Benoist, C., Chambon, P. (1981) "In vivo sequence requirements of the SV40 early promoter region" *Nature* 290:304-310.
Brinster, R. L. et al. (1982) "Regulation of metallothionein-thymidine kinase fusion plasmids injected into mouse eggs" *Nature* 296:39-42.
Capeechi, M. R. (1980) "High efficiency transformation by direct microinjection of DNA into cultured mammalian cells" *Cell* 22(2):479-488.
Clapp, J. F. (1993) "Somatic gene therapy into hematopoietic cells. Current status and future implications" *Clin. Perinatol.* 20(1):155-168.
Cristou, P. et al. (1988) "Stable Transformation of Soybean Callus by DNA-Coated Gold Particles" *Plant Physiol.* 87:671-674.
Curiel, D. T. et al. (1991) "Adenovirus Enhancement of Transferrin-Polylysine-Mediated Gene Delivery" *Proc. Natl. Acad. Sci. USA* 88(19):8850-8854.

Curiel, D. T. et al. (1992) "High-efficiency gene transfer mediated by adenovirus coupled to DNA-polylysine complexes" *Hum. Gen. Ther.* 3(2):147-154.

D'Auria J. C. et al. (2002) "Characterization of an acyltransferase capable of synthesizing benzylbenzoate and other volatile esters in flowers and damaged leaves of *Clarkia breweri*" *Plant Physiol.* 130:466-476.

deBoer, H. A. et al. (1983) "The tac promoter: a functional hybrid derived from the trp and lac promoters" *Proc. Natl. Acad. Sci. U.S.A.* 80(1):21-25.

Eglitis, M. A. et al, (1988) "Retroviral-mediated gene transfer into hemopoietic cells" *Avd. Exp. Med. Biol.* 241:19-27.

Eglitis, M. A., Anderson, W. F. (1988) "Retroviral Vectors for Introduction of Genes into Mammalian Cells" *Biotechniques* 6(7):608-614.

Eihauer, A. et al. (2001) "The FLAG™ Peptide, a Versatile Fusion Tag for the Purification of Recombinant Proteins"*J. Biochem Biophys Methods* 49:455-65.

Fraley, R. T. et al. (1985) "The SEV system: A new disarmed Ti plasmid vector system for plant transformation" *Biotechnology* 3:629-635.

Fynan, E. F. et al. (1993) "DNA Vaccines: Protective Immunizations by Parenteral, Mucosal, and Gene-Gun Inoculations" *Proc. Natl. Acad. Sci. USA,* 90(24):11478-11482.

Gardner, R. C. et al, (1981) "The complete nucleotide sequence of an infectious clone of cauliflower mosaic virus by M13 mp 7 shotgun sequencing" *Nucl. Acids Res.* 9(12): 2871-2888.

Graham, F. L., van der Eb, A. J. (1973) "Transformation of rat cells by DNA of human adenovirus 5" *Virology* 54(02): 536-539.

Herrera-Estrella, L. et al. (1983) "Expression of chimaeric genes transferred into plant cells using a Ti-plasmid-derived vector" *Nature* 303:209-213.

Herrera-Estrella, L. et al. (1984) "Light-inducible and chloroplast-associated expression of a chimaeric gene introduced into *Nicotiana tabacum* using a Ti plasmid vector" *Nature* 310:115-120.

Johnston, S. A., Tang, D. C. (1994) "Gene gun transfection of animal cells and genetic immunization" *Methods Cell. Biol.* 43(A):353-365.

Jones, C. et al. (1995) "Current Trends in Molecular Recognition and Bioseparation" *J. of Chromatography A.* 707:3-22.

Jorgensen, R. A. et al. (1987) T-DNA is organized predominantly in inverted repeat structures in plants transformed with *Agrobacterium tumefaciens* C58 derivatives" *Mol. Gen. Genet.* 207:471-477.

Marcotte, W. R. et al. (1988) "Regulation of a wheat promoter by abscisic acid in rice protoplasts" *Nature* 335:454-457.

Margolin, W. (2000) "Green Fluorescent Protein as a Reporter for Macromolecular Localization in Bacterial Cells" *Methods* 20:62-72.

Murphy, L. R. et al. (2000), "Simplified amino acid alphabets for protein fold recognition and implications for folding" *Protein Eng.* 13:149-52.

Murray, E. E. et al. (1989) "Codon usage in plant genes" *Nucleic Acids Res.* 17(2):477-498.

Potrykus, I. et al. (1985) "Direct gene transfer to cells of a graminaceous monocot" *Mol. Gen. Genet.* 199:183-188.

Puig, O. et al. (2001) "The Tandem Affinity Purification (TAP) Method: A General Procedure of Protein Complex Purification" *Methods* 24:218-29.

Rogers, S. G. et al. (1987) "Improved Vector for plant transformation: expression cassette vectors and new selectable markers" *Meth. in Enzymol.* 153:253-277.

Rogov S. I. and Nekrasov A. N. (2001) "A numerical measure of amino acid residues similarity based on the analysis of their surroundings in natural protein sequences" *Protein Eng.,* 14: 459-463.

Sambrook, J. et al. (1989) Molecular Cloning, A Laboratory Manual, Second Edition, Cold Spring Harbor Press, N.Y., pp. 9.47-9.57.

Sassenfeld, H. M. (1990) "Engineering Proteins for Purification" *TibTech* 8:88-93.

Sheibani, N. (1999) "Prokaryotic Gene Fusion Expression Systems and Their Use in Structural and Functional Studies of Proteins" *Prep. Biochem. & Biotechnol.* 29(0:77-90.

Skerra, A. et al. (1999) "Applications of a Peptide Ligand for Streptavidin: the Strep-tag" *Biomolecular Engineering* 16:79-86.

Smith, C. (1998) "Cookbook for Eukaryotic Protein Expression: Yeast, Insect, and Plant Expression Systems" *The Scientist* 12(22):20.

Smyth, G. K. et al. (2000) "Eukaryotic Expression and Purification of Recombinant Extracellular Matrix Proteins Carrying the Strep II Tag" *Methods in Molecular Biology* 139:49-57.

Spielmann, A. et al. (1986) "T-DNA structure in transgenic tobacco plants with multiple independent integration sites" *Mol. Gen. Genet.* 205:34-41.

Unger, T. F. (1997) "Show Me the Money: Prokaryotic Expression Vectors and Purification Systems" *The Scientist* 11(17):20.

VIIIa-Kamaroff, L. et al. (1978) "A bacterial clone synthesizing proinsulin" *Proc. Natl. Acad. Sci. USA.* 75(8):3727-3731.

Wagner, E. et al. (1992) "Coupling of Adenovirus to Transferrin-Polylysine/DNA Complexes Greatly Enhances Receptor-Mediated Gene Delivery and Expression of Transfected Genes" *Proc. Natl. Acad. Sci. USA* 89(13): 6099-6103, Wong, T. K., Neumann, E. (1982) Electric field mediated gene transfer" *Biochim. Biophys. Res. Commun.,* 107(2): 584-587.

Zatloukal, K. et al. (1992) "Transferrinfection: a highly efficient way to express gene constructs in eukaryotic cells" *Ann. NY. Acad. Sci.* 660:136-153.

We claim:

1. A transgenic plant cell comprising a recombinant polynucleotide that encodes a protein having methyltransferase activity and at least 95% sequence identity to SEQ ID NO: 2.

2. The transgenic plant cell of claim 1, wherein expression of said polynucleotide induces said cell to be resistant or tolerant to an auxin-based herbicide.

3. The transgenic plant cell of claim 1, wherein said polynucleotide comprises SEQ ID NO: 1.

4. The transgenic plant cell of claim 1, said plant cell further comprising a second, heterologous gene that provides said plant cell with tolerance to a second herbicide.

5. The transgenic plant cell of claim 1, wherein said plant cell is a dicotyledonous cell.

6. The transgenic plant cell of claim 1, wherein said plant cell is a monocotyledonous cell.

7. A transgenic plant comprising a plurality of cells according to claim 1, wherein expression of said polynucleotide renders said plant tolerant to an auxin-based herbicide.

8. A method of controlling weeds, said method comprising over-spraying/applying a composition comprising an auxin-based herbicide to an area containing a plant and a weed, said plant comprising a plurality of plant cells according to claim 1.

9. The method of claim 8, wherein said plant is soybean, corn, *Arabidopsis*, tobacco, cotton, canola, rice, wheat, turf, alfalfa, clover, pasture grasses, a fruit plant, a vegetable or an ornamental plant.

10. The method of claim 8, wherein said plant further comprises a glyphosate resistance gene, and said method further comprises applying glyphosate to said plant and to said weed.

11. The method of claim 10, said plant further comprising a third herbicide resistance gene, and said method further comprising applying a third herbicide to said plant and to said weed.

12. A transgenic plant comprising a heterologous polynucleotide that encodes a methyltransferase comprising SEQ ID NO: 2, said transgenic plant being resistant to an auxin-based herbicide.

13. The transgenic plant of claim 12, said plant further comprising at least one additional herbicide resistance gene.

14. The transgenic plant of claim 12, wherein said plant further comprises an insect-resistance gene derived from an organism selected from the group consisting of *Bacillus ihuringiensis*, Photorhabdus, and Xenorhabdus.

15. The transgenic plant of claim 12, wherein said plant further comprises a gene for an agronomic trait selected from the group consisting of fungal resistance, stress tolerance, increased yield, improved oil profile, improved fiber quality, viral resistance, delayed ripening, cold tolerance, and salt tolerance.

16. The transgenic plant of claim 12, wherein said plant comprises a biological insecticide derived from a source selected from the group consisting of *Bacillus popilliae, B. sphaericus, B. thuringiensis* subsp. *aizawai, B. thuringiensis* subsp. *kurstaki, B. thuringiensis* subsp. *tenebrionis, Beauveria bassiana, Cydia pomonella* granulosis virus, Douglas fir tussock moth NPV, gypsy moth NPV, *Helicoverpa zea* NPV, Indian meal moth granulosis virus, *Metarhizium anisopliae, Nosema locustae, Paecilomyces fumosoroseus, P. lilacinus, Photorhabdus luminescens, Spodoptera exigua* NPV, trypsin modulating oostatic factor, *Xenorhabdus nematophilus*, and *X bovienii*.

17. The transgenic plant of claim 12, wherein said plant comprises a plant incorporated protectant insecticide selected from the group consisting of Cry1Ab, Cry1Ac, Cry1F, Cry1A.105, Cry2Ab2, Cry3A, mir Cry3A, Cry3Bb1, Cry34, Cry35, and VIP3A.

18. The transgenic plant of claim 12, wherein said plant is a monocot or a dicot.

19. A seed comprising the plant cell of claim 1.

20. A plant grown from the seed of claim 19.

21. A regenerable part, progeny, or asexual propagate of the plant of claim 12 comprising said heterologous polynucleotide.

22. A method of selecting for a transformed plant cell comprising subjecting a plurality of plant cells to transformation with a polynucleotide encoding a polypeptide comprising SEQ ID NO: 2, growing said cells in a composition comprising a concentration of an auxin-based herbicide that permits transformed cells expressing said polynucleotide to grow while killing or inhibiting the growth of nontransformed cells.

23. The method of claim 22, wherein said method is used for selecting a transformed plant.

24. A method of controlling weeds in a field comprising planting seed of at least one transgenic plant in a field, said seed comprising a recombinant polynucleotide encoding a polypeptide comprising SEQ ID NO: 2, and applying a composition comprising an auxin-based herbicide to at least a portion of said field.

25. The method of claim 24, wherein said plant is resistant to a second herbicide selected from the group consisting of glyphosate, glufosinate, imazethapyr, chlorsulfuron, dicamba, mesotrione, isoxaflutole, and butafenacil.

26. The method of claim 24, wherein said plant is a monocot.

27. The method of claim 26, wherein said monocot is selected from the group consisting of corn, rice, wheat, barley, rye, warm and cool-season turf grass, oats, sorghum, and pasture grasses.

28. The method of claim 24, wherein said first herbicide is an auxin-based and said plant is a dicot.

29. The method of claim 24, wherein said plant is a dicot and is selected from the group consisting of cotton, tobacco, canola, and soybean.

30. The method of claim 24, wherein said method comprises applying a second herbicide and said plant is resistant to said second herbicide.

31. The method of claim 30, wherein said auxin-based herbicide and a second herbicide are applied sequentially.

32. The method of claim 30, wherein said auxin-based herbicide and a second herbicide are applied concurrently.

33. The method of claim 24, wherein said plant is resistant to glyphosate.

34. The method of claim 33, wherein said glyphosate resistance is conferred by a polynucleotide encoding EPSPS (5-enolpyruvylshikimate-3-phosphate synthase) or GAT.

35. An isolated vector comprising a promoter operably linked to a polynucleotide encoding SEQ ID NO: 2; or a fragment of SEQ ID NO: 2 having methyltransferase activity.

36. The vector of claim 35, wherein said promoter is a plant promoter.

37. The vector of claim 35, comprising a promoter selected from a cassava vein mosaic virus promoter, CaMV 35S promoter, Figwort Mosaic Virus promoter, rice actin promoter, phaseolin promoter, *Arabidopsis thaliana* Ubiquitin 10 promoter, maize ubiquitin promoter, *Arabidopsis thaliana* Act2 promoter, *Arabidopsis thaliana* Ubiquitin 11 promoter, and *Arabidopsis thaliana* Ubiquitin 3 promoter.

38. The transgenic plant according to claim 2, wherein said auxin-based herbicide is 2,4-Dichlorophenoxyacetic acid (2,4-D).

39. The transgenic plant according to claim 7, wherein said auxin-based herbicide is 2,4-Dichlorophenoxyacetic acid (2,4-D).

40. The transgenic plant according to claim 12, wherein said auxin-based herbicide is 2,4-D.

* * * * *

UNITED STATES PATENT AND TRADEMARK OFFICE
CERTIFICATE OF CORRECTION

PATENT NO. : 8,404,933 B2
APPLICATION NO. : 12/701973
DATED : March 26, 2013
INVENTOR(S) : Feng Chen et al.

It is certified that error appears in the above-identified patent and that said Letters Patent is hereby corrected as shown below:

Title Page

Abstract (57),
Lines 5-6, "plants have been" should read --plants that have been--.

In the Specification

Column 4,
Line 6, "—O(CH$_2$)—CH$_2$—, or" should read -- —O(CH$_2$)$_n$CH$_2$—, or--.
Line 14, "alkoxy," should read --C$_1$-C$_4$ alkoxy,--.

Column 5,
Line 49, "and —(CH$_2$)$_2$—O—(CH$_2$)$_2$—," should read --and —(CH$_2$)$_2$O(CH$_2$)$_2$—,--.

Column 10,
Line 17, "with in a" should read --within a--.

Column 13,
Line 1, "vendors such as such as STRATAGENE" should read
    --vendors such as STRATAGENE--.

Column 17,
Lines 58-59, "PtJBMTm3 also be" should read --PtJBMTm3 can also be--.

Column 18,
Line 10, "marker" should read --marker.--.

Column 22,
Line 56, "Capeechi," should read --Capecchi,--.

Signed and Sealed this
Twelfth Day of November, 2013

Teresa Stanek Rea
*Deputy Director of the United States Patent and Trademark Office*

In the Claims

Column 29,
Lines 63-64, "*ihuringiensis*," should read --*thuringiensis*,--.